US012616812B2

(12) United States Patent
Ramanan

(10) Patent No.: US 12,616,812 B2
(45) Date of Patent: May 5, 2026

(54) METHODS AND APPARATUS FOR TREATING RESPIRATORY DISORDERS

(71) Applicant: ResMed Pty Ltd, Bella Vista (AU)

(72) Inventor: Dinesh Ramanan, Sydney (AU)

(73) Assignee: ResMed Pty Ltd (AU)

( * ) Notice: Subject to any disclaimer, the term of this patent is extended or adjusted under 35 U.S.C. 154(b) by 833 days.

(21) Appl. No.: 17/875,862

(22) Filed: Jul. 28, 2022

(65) Prior Publication Data

US 2022/0370745 A1     Nov. 24, 2022

Related U.S. Application Data

(63) Continuation of application No. 16/071,334, filed as application No. PCT/AU2017/050081 on Feb. 1, 2017, now Pat. No. 11,433,201.

(30) Foreign Application Priority Data

Feb. 2, 2016     (AU) ................................ 2016900329

(51) Int. Cl.
A61M 16/06          (2006.01)
A61B 5/00            (2006.01)
(Continued)

(52) U.S. Cl.
CPC ......... A61M 16/024 (2017.08); A61B 5/4836 (2013.01); A61M 16/0066 (2013.01);
(Continued)

(58) Field of Classification Search
CPC ..... A61B 5/0205; A61B 5/02405; A61B 5/08; A61B 5/087; A61B 5/0871; A61B 5/091;
(Continued)

(56) References Cited

U.S. PATENT DOCUMENTS

| | | |
|---|---|---|
| 4,944,310 A | 7/1990 | Sullivan |
| 7,866,944 B2 | 1/2011 | Kenyon et al. |

(Continued)

FOREIGN PATENT DOCUMENTS

| | | |
|---|---|---|
| EP | 2000090 A2 | 12/2008 |
| EP | 2806932 A1 | 12/2014 |

(Continued)

OTHER PUBLICATIONS

PCT International Search Report mailed May 15, 2017.
(Continued)

*Primary Examiner* — Annette Dixon
(74) *Attorney, Agent, or Firm* — Botos Churchill IP Law LLP

(57)          ABSTRACT

Methods and apparatus infer or indicate sleep stage(s) of a patient from a respiratory flow rate signal of the patient. The method may include applying a plurality of detection pathways to a signal representing a respiratory flow rate of the patient, wherein each detection pathway is configured to generate start events and end events indicating start times and end times of episodes respectively of a corresponding sleep stage, wherein each start event and each end event has a priority; and combining the start events and end events based on their priorities to produce an indication of the sleep stage of the patient. The apparatus may include a sensor configured to generate a signal representing a property of a flow of air within a patient interface; and a processor configured to implement a method of inferring a sleep stage of the patient from the signal.

27 Claims, 24 Drawing Sheets

(51) Int. Cl.
*A61M 16/00* (2006.01)
*A61M 16/16* (2006.01)

(52) U.S. Cl.
CPC ........ *A61M 16/0683* (2013.01); *A61M 16/16*
(2013.01); *A61M 2016/003* (2013.01); *A61M
2205/07* (2013.01); *A61M 2205/52* (2013.01);
*A61M 2230/40* (2013.01)

(58) Field of Classification Search
CPC ..... A61B 5/097; A61B 5/4809; A61B 5/4812;
A61B 5/4815; A61B 5/4818; A61B
5/4836; A61B 5/7267; A61B 5/7282;
A61B 5/746; A61B 5/7475; A61M 16/00;
A61M 16/0003; A61M 16/0009; A61M
16/0051; A61M 16/0057; A61M 16/0066;
A61M 16/0069; A61M 16/024; A61M
16/026; A61M 16/0461; A61M 16/0633;
A61M 16/0666; A61M 16/0683; A61M
16/1055; A61M 16/16; A61M 16/20;
A61M 2016/0027; A61M 2016/003;
A61M 2016/0036; A61M 2021/0083;
A61M 2021/0088; A61M 21/00; A61M
2202/0007; A61M 2202/0208; A61M
2205/07; A61M 2205/15; A61M 2205/18;
A61M 2205/3327; A61M 2205/3331;
A61M 2205/3523; A61M 2205/42; A61M
2205/50; A61M 2205/502; A61M
2205/505; A61M 2205/52; A61M
2205/8206; A61M 2230/00; A61M
2230/40; A61M 2230/60; A61N 1/3601;
A61N 1/36514; F04B 45/043; F04B
45/047; F16K 1/18; Y02A 90/10
See application file for complete search history.

(56) References Cited

U.S. PATENT DOCUMENTS

| | | | |
|---|---|---|---|
| 8,069,852 B2 | 12/2011 | Burton et al. |
| 8,636,479 B2 | 1/2014 | Kenyon et al. |
| 8,638,014 B2 | 1/2014 | Sears |
| 8,733,349 B2 | 5/2014 | Bath et al. |

| | | | |
|---|---|---|---|
| 9,108,009 B2 | 8/2015 | Rapoport et al. | |
| 11,134,887 B2 | 10/2021 | Pituch | |
| 11,433,201 B2 * | 9/2022 | Ramanan .......... A61M 16/0683 | |
| 2005/0012622 A1 | 1/2005 | Sutton | |
| 2005/0061320 A1 * | 3/2005 | Lee ..................... A61N 1/36514 | |
| | | | 128/204.23 |
| 2005/0085738 A1 | 4/2005 | Stahmann et al. | |
| 2011/0018720 A1 | 1/2011 | Rai et al. | |
| 2012/0179061 A1 * | 7/2012 | Ramanan ............. A61B 5/7475 | |
| | | | 128/204.23 |
| 2012/0323085 A1 | 12/2012 | Takeda | |
| 2015/0080642 A1 * | 3/2015 | Fox ........................ A61B 5/746 | |
| | | | 600/26 |
| 2015/0164682 A1 | 6/2015 | Remmers et al. | |
| 2015/0250963 A1 | 9/2015 | Ramanan | |
| 2015/0267695 A1 * | 9/2015 | Marsh ................... F04B 45/043 | |
| | | | 128/205.24 |
| 2019/0090860 A1 | 3/2019 | Shinar et al. | |

FOREIGN PATENT DOCUMENTS

| | | | |
|---|---|---|---|
| JP | 4750032 B2 | 5/2011 |
| WO | 2006066337 | 6/2006 |
| WO | 2008039979 A2 | 4/2008 |
| WO | 2008138040 A1 | 11/2008 |
| WO | 2011006199 A1 | 1/2011 |
| WO | 2013020167 A1 | 2/2013 |
| WO | 2013133889 A1 | 9/2013 |
| WO | 2013152403 | 10/2013 |
| WO | 2013172722 A1 | 11/2013 |
| WO | 2014047310 A1 | 3/2014 |
| WO | 2015103558 A1 | 7/2015 |
| WO | 2015103694 A1 | 7/2015 |
| WO | 2015120522 A1 | 8/2015 |
| WO | 2015131219 | 9/2015 |

OTHER PUBLICATIONS

Supplementary EP Search Report for EP Application No. 17746640.6 dated Aug. 14, 2019.
The Extended European Search Report for European Patent Application No. 21166444.6, Oct. 22, 2021.
West, John B., "Respiratory Physiology", Lippincott Williams & Wilkins, 9th Edition published 2012.
Examination Report issued in corresponding New Zealand Patent Application No. 784397, mailed Mar. 6, 2024, 4 pages.

* cited by examiner

Nasal cavity

Oral cavity

Larynx

Vocal folds

Oesophagus

Trachea

Bronchus

Lung

Heart

Diaphragm

Alveolar sacs

5000

7200

Calculate breath variance features — 7210

Transform breath variance features — 7220

Combine transformed variance features — 7225

Calculate difference features — 7230

Calculate trend features — 7240

Calculate thresholds — 7250

Sleep onset detector — 7260

REM sleep detector — 7270

Wakefulness detector — 7280

7400

7410

Wait for
ventilation ratio
to stabilise

7420

Slow_Var_xform
stable for a long
period?

N

Y

7430

Slow_Var_xform stable
for a long period without a significant
unstable interval in that period?

N

Y

7440

Slow_Var_xform not very
unstable for a long period without a
significant very unstable interval in
that period?

N

Y

7450

Issue
NREM start
event

METHODS AND APPARATUS FOR TREATING RESPIRATORY DISORDERS

1 CROSS-REFERENCE TO RELATED APPLICATIONS

The present application is a continuation application of U.S. patent application Ser. No. 16/071,334, filed Jul. 19, 2018, which is a national phase entry under 35 U.S.C. § 371 of International Application No. PCT/AU2017/050081 filed Feb. 1, 2017, published in English, which claims priority from Australian Provisional Patent Application No. AU 2016900329, filed Feb. 2, 2016, all of which are incorporated herein by reference.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

BACKGROUND OF THE TECHNOLOGY

2.1 Field of the Technology

The present technology relates to one or more of the detection, diagnosis, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

2.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of air at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of air at a positive pressure of about 10 $cmH_2O$.

2.2.3.2 Respiratory Pressure Therapy (RPT) Device

An RPT device is typically a generator of a flow of air at a pressure above ambient. Air pressure generators are known in a range of applications, e.g. industrial-scale ventilation systems. However, air pressure generators for medical applications have particular requirements not fulfilled by more generalised air pressure generators, such as the reliability, size and weight requirements of medical devices.

2.2.3.3 Humidifier

Delivery of a flow of air without humidification may cause drying of airways. The use of a humidifier with an RPT device and the patient interface produces humidified air that minimizes drying of the nasal mucosa and increases patient airway comfort. In addition in cooler climates, warm air applied generally to the face area in and about the patient interface is more comfortable than cold air.

2.2.3.4 Data Management

Data management in a treatment system is intended to communicate the patient's therapy data to an external or remote system for analysis, display, or storage. Typically, data management takes the form of a wired or wireless connection from an RPT device to a remote server via a local or wide area network such as the Internet. Various parameters of the patient's therapy are transmitted over the network connection to the server on request or at predetermined intervals. The server hosts processes configured to analyse the data to extract summary information for storage or display to the patient or a clinician responsible for the patient's therapy.

2.2.4 Sleep Stage Inference

While RPT devices may typically be configured to detect SDB events such as apneas and hypopneas in real time, they do not typically determine or provide more detailed information about the patient's sleep while on respiratory pressure therapy.

In particular, it is of interest to know when the patient went to sleep, when the patient awoke, and what stages of sleep the patient passed through in the meantime. A complete representation of the various sleep stages (or sleep states; the terms are generally synonymous) passed through by a patient during a sleep session is called a hypnogram. One example application of a hypnogram is the computation of an index of severity of SDB known as the apnea-hypopnea index (AHI). AHI, which is usually calculated as the total number of apneas and hypopneas divided by the length of the sleep session, is a widely-used screening, diagnostic, and monitoring tool for SDB. However, such calculation tends to underestimate the AHI, since for significant periods during the session the patient may not have been asleep. The result is that a patient or clinician tends to get an overly optimistic picture of the efficacy of the patient's therapy if conventional AHI calculation is employed.

A more accurate method of calculating the AHI is to divide the number of apneas and hypopneas by the number of hours the patient was asleep during the session. To compute the AHI in this way requires knowledge of when the patient was asleep, knowledge which may be obtained from a hypnogram. However, inferring sleep stage purely from respiratory flow rate has proven to be a difficult task, with consequent effects on the accuracy of AHI calculation and hence AHI-based monitoring of patients on CPAP therapy. A need therefore exists to develop improved methods and apparatus for inferring stages of a CPAP therapy patient's sleep in order to more accurately assess the patient's condition and the efficacy of the applied therapy.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first form of the present technology relates to apparatus used in the diagnosis, amelioration, treatment or prevention of a respiratory disorder.

Another form of the present technology relates to methods used in the diagnosis, amelioration, treatment or prevention of a respiratory disorder.

Aspects of certain forms of the present technology include methods and/or apparatus for inferring stages of a CPAP therapy patient's sleep from the patient's respiratory flow rate signal. The apparatus may be an RPT device or a remote computing device in communication with the RPT device.

One form of the present technology comprises methods and apparatus for parallel detection of start and end events of different sleep stages from the respiratory flow rate signal, and combining the start and events of each stage taking into account the priority of each kind of event to produce an indication of a sleep stage of a patient.

Another form of the present technology comprises methods and apparatus for distinguishing respiratory event sleep from wakefulness based on the respiratory flow rate signal, and combining the start and events of respiratory event sleep and wakefulness taking into account the priority of each kind of event to produce an indication of a sleep stage.

Some versions of the present technology may include a method of indicating a sleep stage of a patient. The method may include applying, in one or more processors, a plurality of detection pathways to a signal representing a respiratory flow rate of the patient. Each detection pathway of the plurality may be configured to generate start events and end events indicating start times and end times respectively of episodes of a corresponding sleep stage. Each start event and each end event of such events has a priority. The method may include combining, in the one or more processors, the start events and end events based on their priorities to produce an indication of a sleep stage of the patient.

In some versions, the one or more processors may be configured to resolve detection collisions between sleep stages detected by different detection pathways. The combining may include disregarding a detected stage of a lower priority in favor of a detected sleep stage of higher priority. The one or more processors may be configured to indicate the sleep stage from a set of stages including any two or more of: deep sleep; Long-term awake type 2; respiratory event sleep (RES); Long-term awake type 1; Short-term awake; and REM.

In some versions, the method may include generating a supply of air at positive pressure to an airway of the patient; and altering a treatment pressure of the supply of air based on the indication of the sleep stage of the patient. The method may include storing the indication of the sleep stage of the patient in a hypnogram. In some versions, the combining of the start events and end events may include: storing the start events and end events in time order; and consolidating the start events and end events into a hypnogram based on their priorities. In some versions, one detection pathway is a respiratory event pathway configured to generate start events and end events indicating start times and end times respectively of episodes of respiratory event sleep. The respiratory event pathway may be configured to generate a respiratory event sleep start event on detecting a series of respiratory events in close succession. The respiratory events may be one or more of apneas, hypopneas, and respiratory event-related arousals (RERAs). Each of the hypopneas may be an obstructive hypopnea.

The respiratory event pathway may be configured to generate a respiratory event sleep end event upon not detecting a respiratory event for a timeout threshold. One detection pathway may be a breathing stability pathway configured to generate start events and end events indicating start times and end times respectively of episodes of one or more of: non-respiratory-event sleep, and wakefulness. In some cases, non-respiratory event sleep may be one or more of: REM sleep, and deep sleep. The breathing stability pathway may include a REM sleep detector configured to generate a REM start event on detecting short-term and medium-term variation in breath features, but long-term stability of the breath features. The breathing stability pathway may include a sleep onset detector configured to generate a deep sleep start event on detecting a transition of breath features from highly variable to semi-stable. The breathing stability pathway may include a wakefulness detector configured to generate start events and end events indicating start times and end times respectively of episodes of one or more of: short-term awake; and long-term awake. The wakefulness detector may be configured to generate a short-term awake start event on detecting large short-term variation in breath features. The wakefulness detector may be configured to generate a long-term awake start event on detecting large long-term variation in breath features. The wakefulness detector may be configured to generate start events and end events indicating start times and end times respectively of episodes of two types of long-term awake. The wakefulness detector may be configured to generate a long-term awake start event of a second type on detecting medium-term variability of a breath feature.

In some versions, one detection pathway may be a respiratory event pathway configured to generate start events and end events indicating start times and end times respectively of episodes of respiratory event sleep. One detection pathway may be a breathing stability pathway configured to generate start events and end events indicating start times and end times respectively of episodes of deep sleep. In some cases, deep sleep events may have a higher priority than respiratory event sleep events.

Some versions of the present technology may include a computer processor-readable memory storage apparatus having processor-executable instructions encoded thereon which, when executed by a processor, cause the processor to perform a method of indicating a sleep stage of a patient. The method may include any of such methods described herein.

Some versions of the present technology may include apparatus including a sensor and one or more processors. The sensor may be configured to generate a signal representing a property of a flow of air within a patient interface where the patient interface may be configured to engage with an entrance to an airway of a patient. The one or more processors may be coupled with the computer processor-readable memory storage apparatus. The one or more processors may be configured to indicate a sleep stage of the patient from the signal according to the processor-executable instructions encoded on the computer processor-readable memory storage apparatus. The apparatus may include a pressure generator configured to generate a supply of air at positive pressure to an airway of the patient via the patient interface over an air circuit. The one or more processors may be configured to control the supply of air based on the sleep stage indicated.

Some versions of the present technology may include apparatus including a sensor and one or more processors. The sensor may be configured to generate a signal representing a property of a flow of air within a patient interface. The patient interface may be configured to engage with an entrance to an airway of a patient. The one or more processors may be configured to indicate a sleep stage of the patient from the signal. The one or more processors may be configured to apply a plurality of detection pathways to the signal, wherein each detection pathway may be configured to generate start events and end events indicating start times and end times respectively of episodes of a corresponding sleep stage. Each start event and each end event may have a priority. The one or more processors may be configured to combine the start events and end events based on their priorities to produce an indication of a sleep stage of the patient.

In some versions, the sensor may be located within the patient interface and the property may be pressure. The one or more processors may be located within the patient interface. The one or more processors may be located in a remote external computing device configured to communicate with the patient interface. The apparatus may include a pressure generator configured to generate a supply of air at positive pressure to an airway of the patient via the patient interface over an air circuit. The apparatus may include a central controller configured to control the pressure generator. The one or more processors may be the central controller. The one or more processors may be located in a remote external computing device configured to communicate with the central controller. The sensor may be located within the pressure generator, and the property may be flow rate. The sensor may be located within the air circuit, and the property is flow rate. The one or more processors may be configured to resolve detection collisions between sleep stages detected by different detection pathways.

In some versions, to combine the start events and end events based on their priorities, the one or more processors may be configured to disregard a detected stage of a lower priority in favor of a detected sleep stage of higher priority. The one or more processors may be configured to indicate the sleep stage from a set of stages including any two or more of: deep sleep; Long-term awake type 2; respiratory event sleep (RES); Long-term awake type 1; Short-term awake; and REM. The apparatus may also optionally include the patient interface.

Some versions of the present technology may include a system. The system may include means for generating a signal representing a property of a flow of air within a means for engaging with an entrance to an airway of a patient. The system may include means for applying a plurality of detection pathways to the signal, wherein each detection pathway is configured to generate start events and end events indicating start times and end times respectively of episodes of a corresponding sleep stage, wherein each start event and each end event has a priority. The system may include means for combining the start events and end events based on their priorities to produce an indication of a sleep stage of the patient. The system may optionally include the means for engaging with an entrance to an airway of the patient.

The methods/systems/devices/apparatus described herein can provide improved functioning in a processor, such as of a processor of a specific purpose computer, respiratory monitor and/or a respiratory pressure therapy apparatus. Moreover, the methods/devices/apparatus can provide improvements in the technological field of automated management, monitoring and/or treatment of respiratory conditions, including, for example, sleep disordered breathing. For example, such functioning may improve detection of sleep stages over other methodologies.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE DRAWINGS

The present technology is illustrated by way of example, and not by way of limitation, in the figures of the accompanying drawings, in which like reference numerals refer to similar elements including.

4.1 Treatment Systems

4.2 Respiratory System and Facial Anatomy

Figure 1:
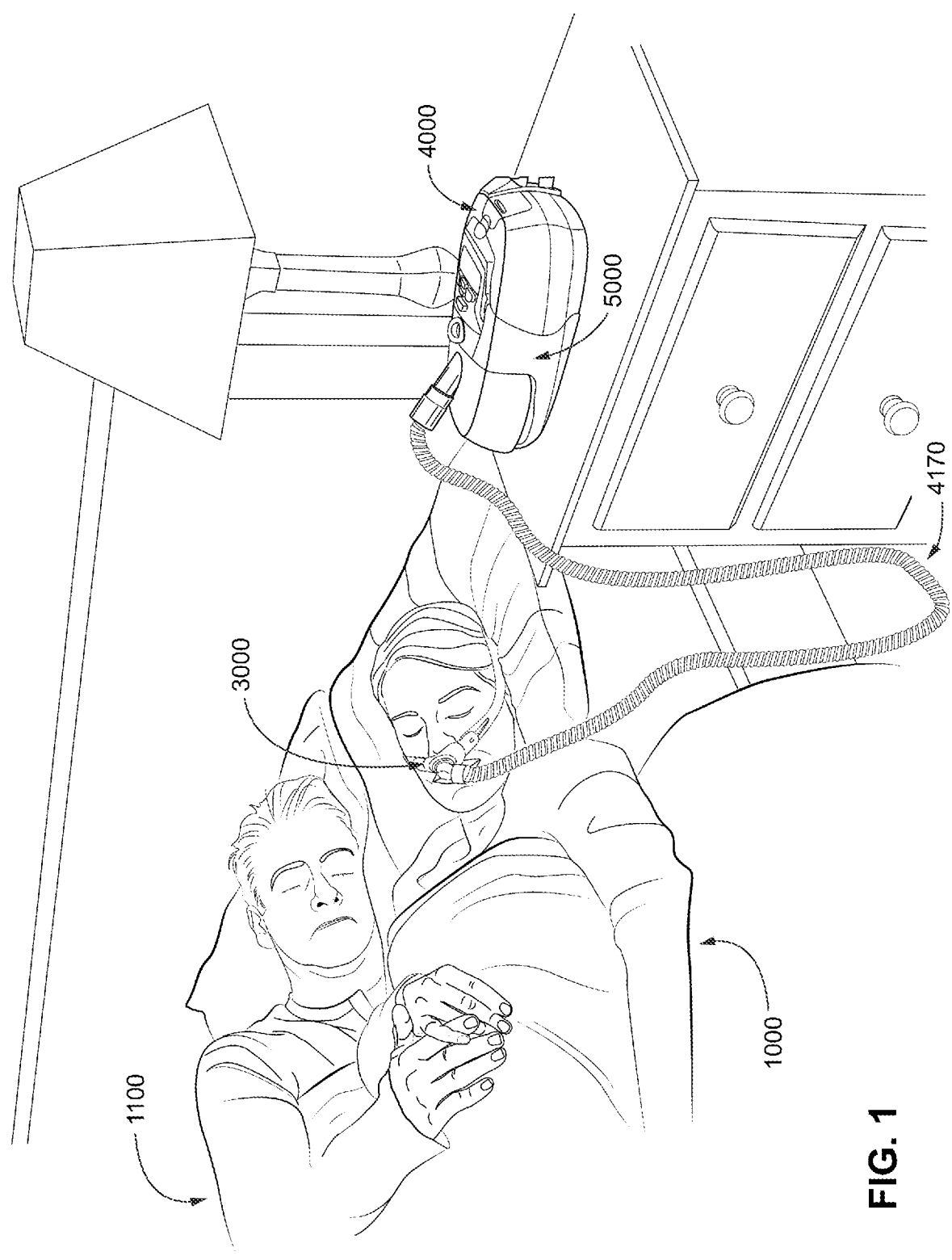
FIG. 1 shows a system including a patient 1000 wearing a patient interface 3000, in the form of a nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown.
Figure 2:
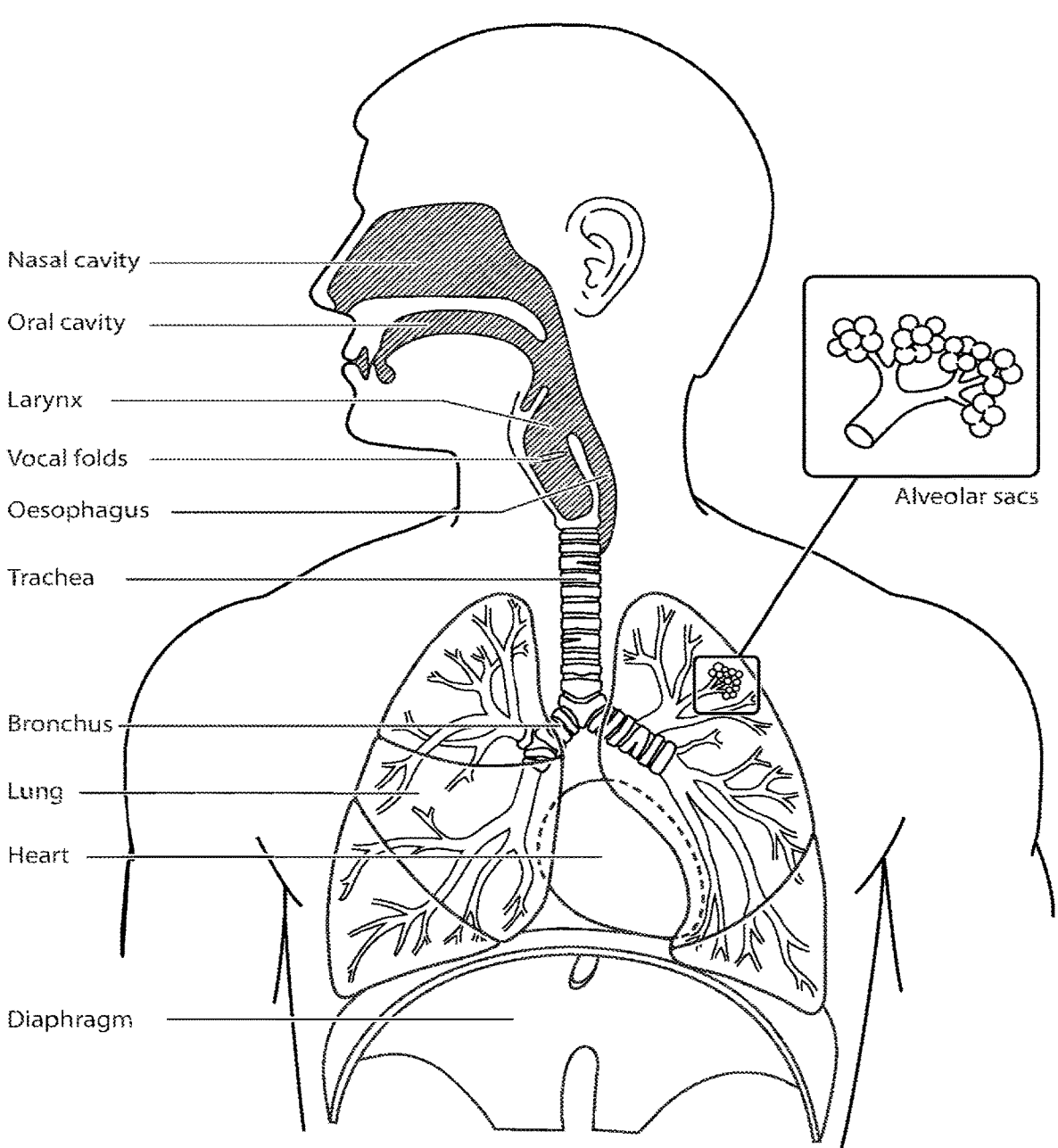

FIG. 2 shows an overview of a human respiratory system including the nasal and oral cavities, the larynx, vocal folds, oesophagus, trachea, bronchus, lung, alveolar sacs, heart and diaphragm.

4.3 Patient Interface

Figure 3:
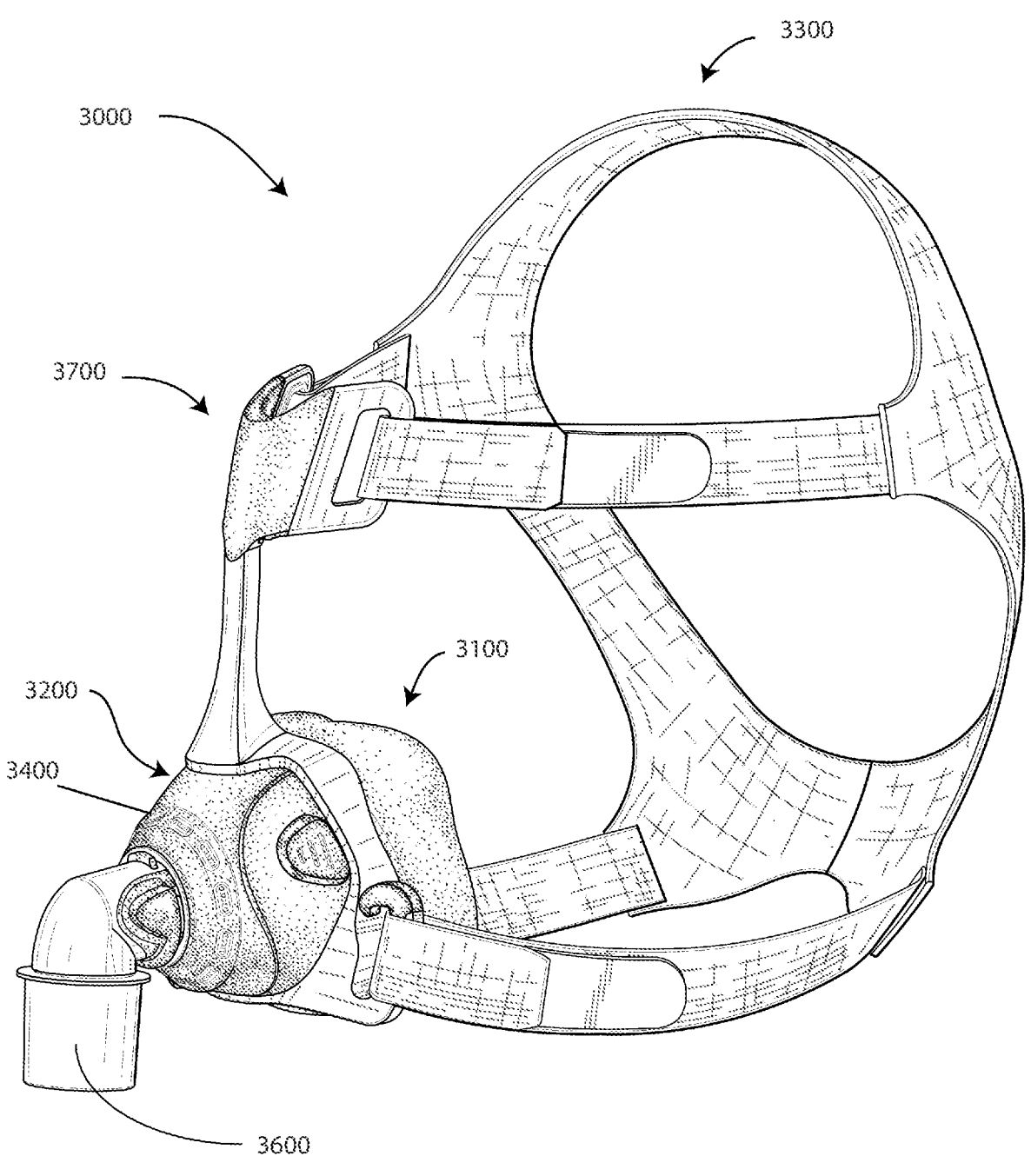

FIG. 3 shows a patient interface in the form of a nasal mask in accordance with one form of the present technology.

4.4 RPT Device

Figure 4A:
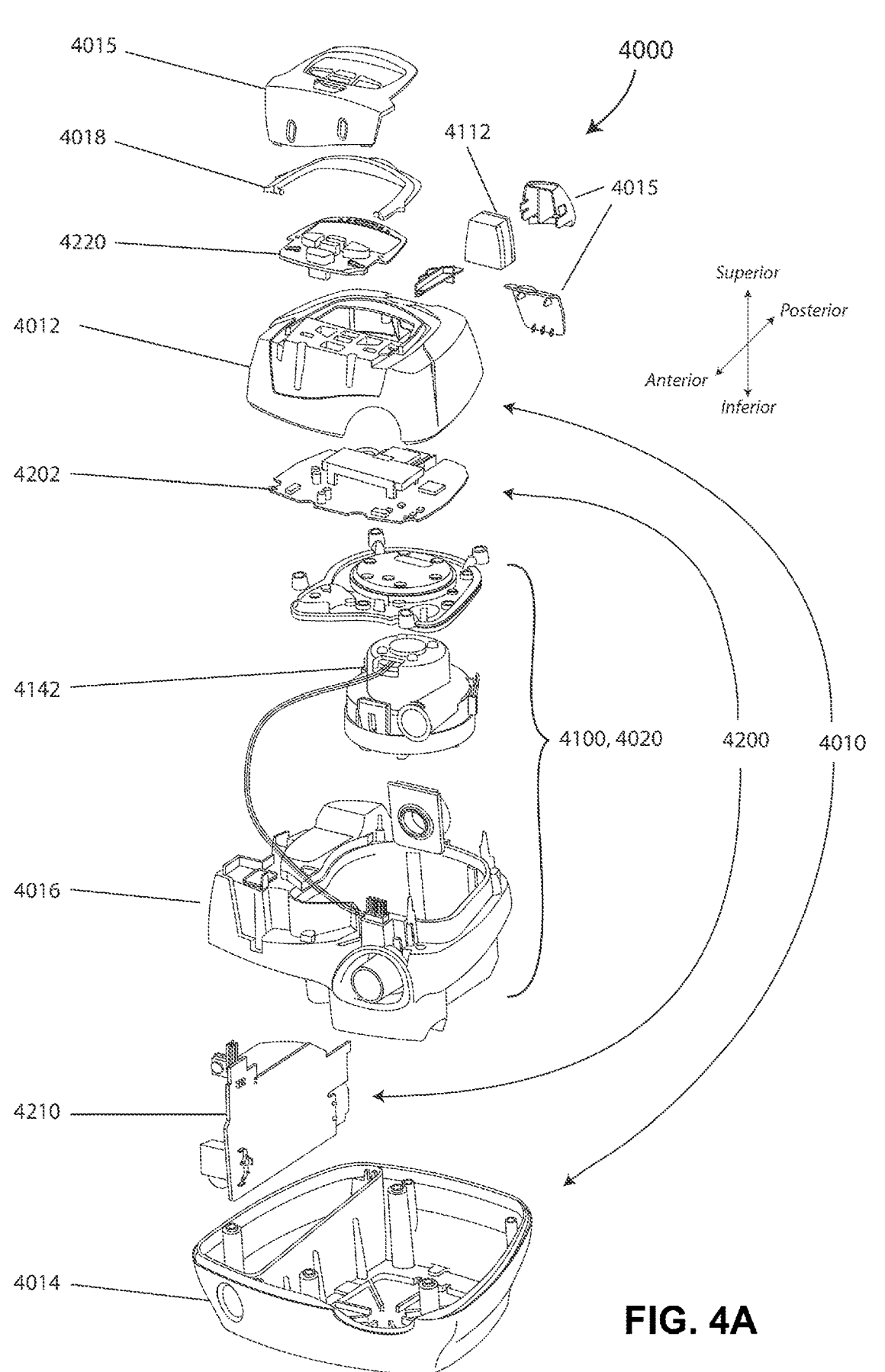

FIG. 4A shows an RPT device in accordance with one form of the present technology.

Figure 4B:
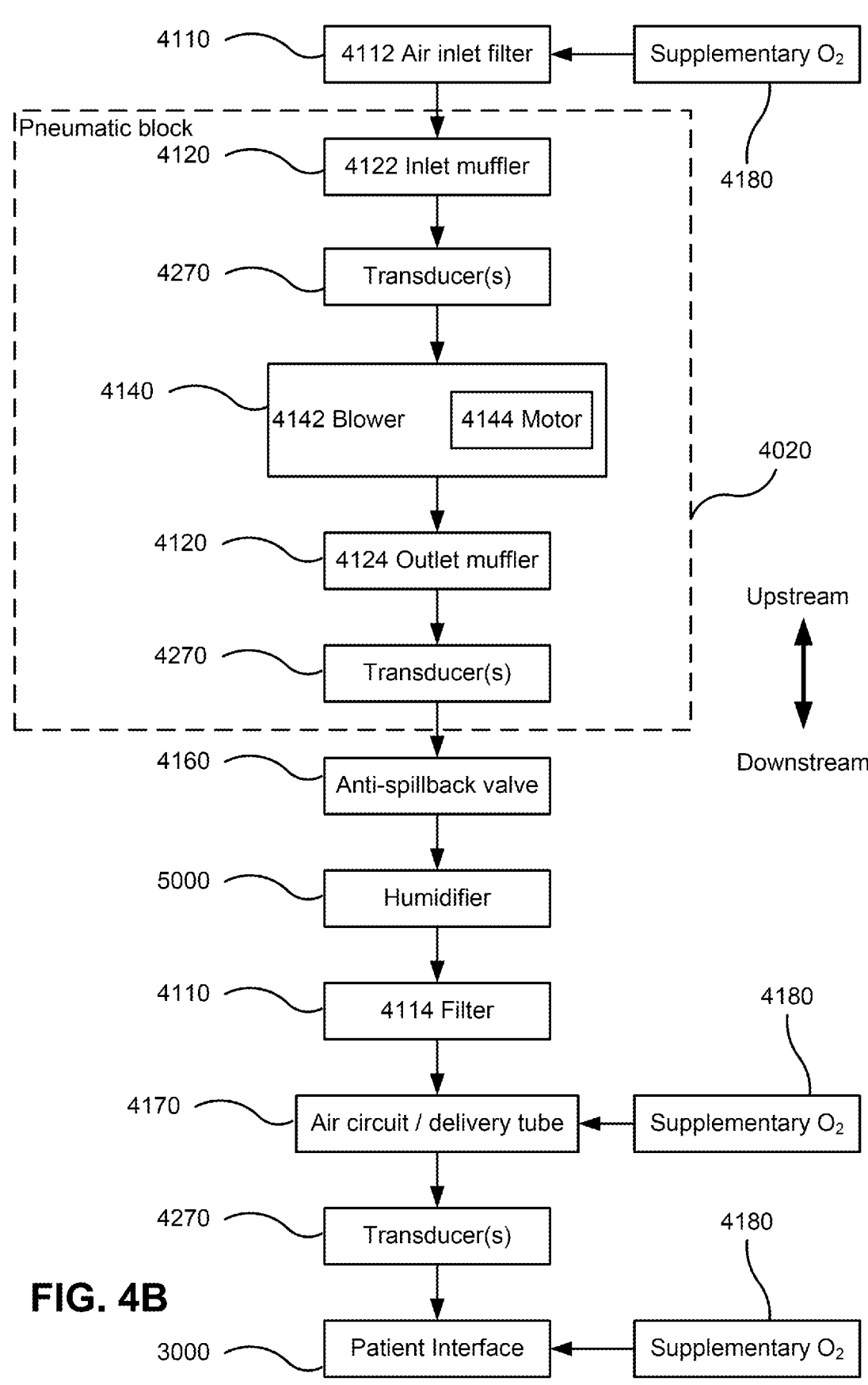

FIG. 4B is a schematic diagram of the pneumatic path of an RPT device in accordance with one form of the present technology. The directions of upstream and downstream are indicated.

Figure 4C:
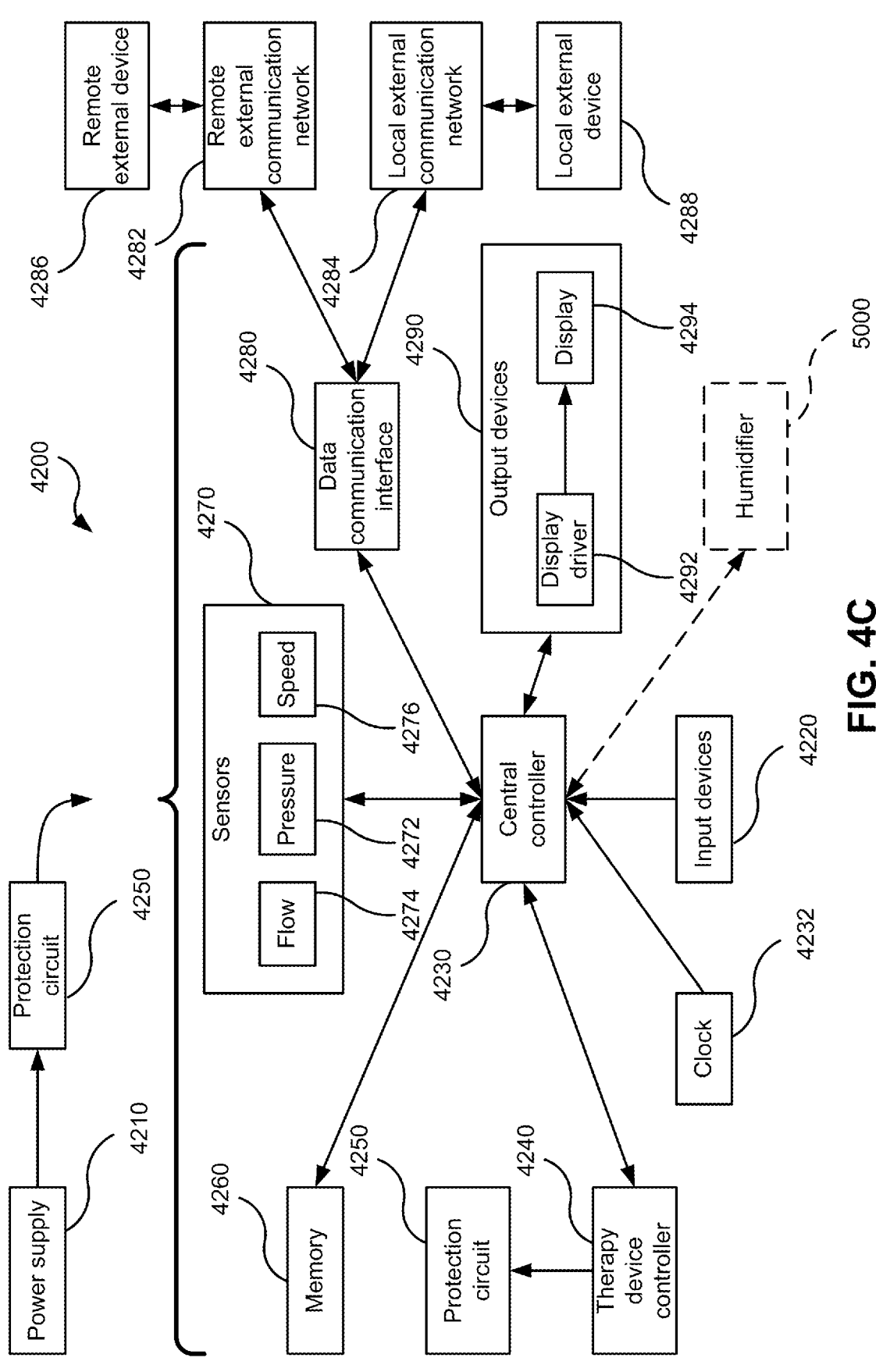

FIG. 4C is a schematic diagram of the electrical components of an RPT device in accordance with one form of the present technology.

Figure 4D:
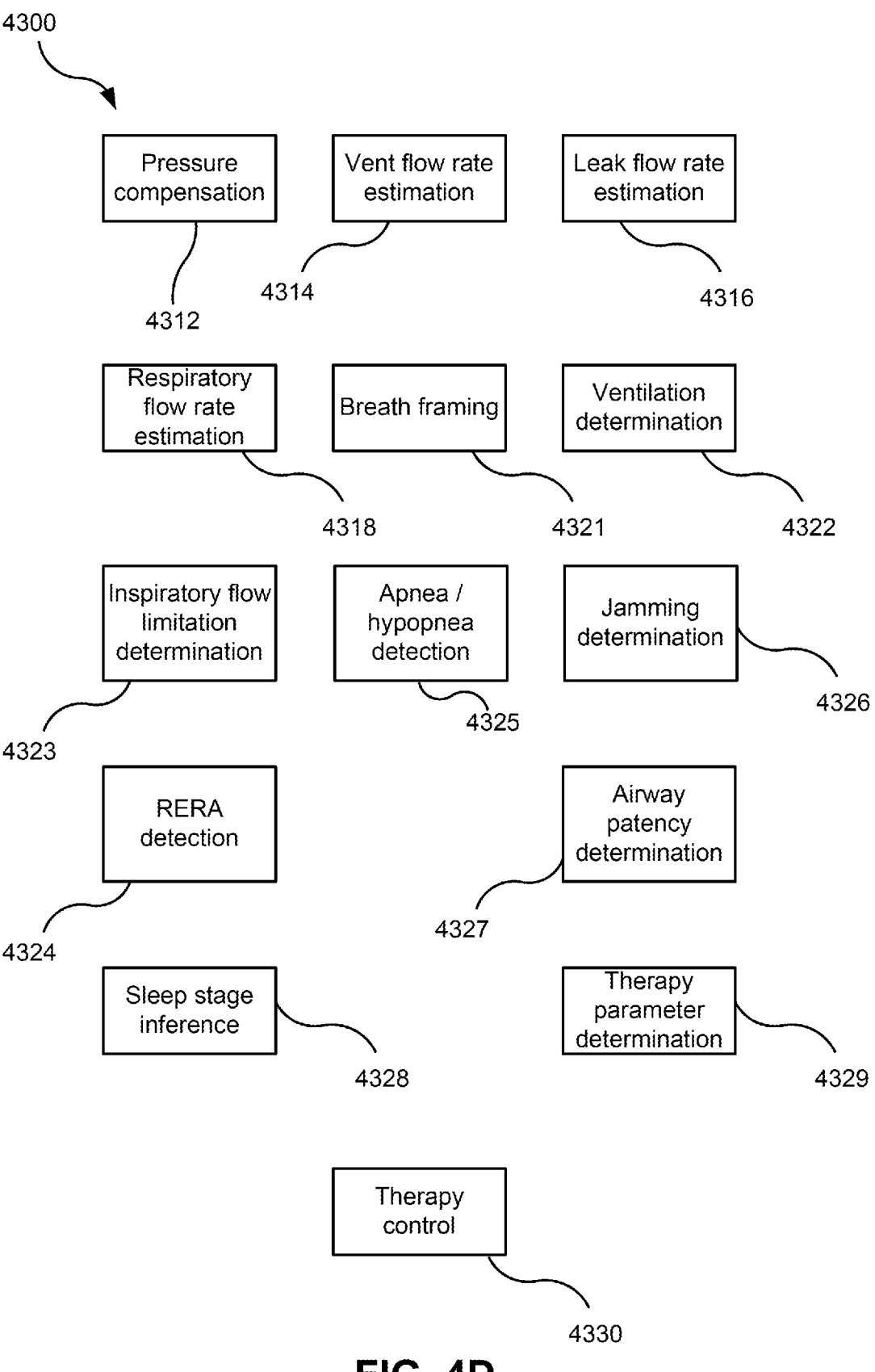

FIG. 4D is a schematic diagram of the algorithms implemented in an RPT device in accordance with one form of the present technology.

4.5 Humidifier

Figure 5:
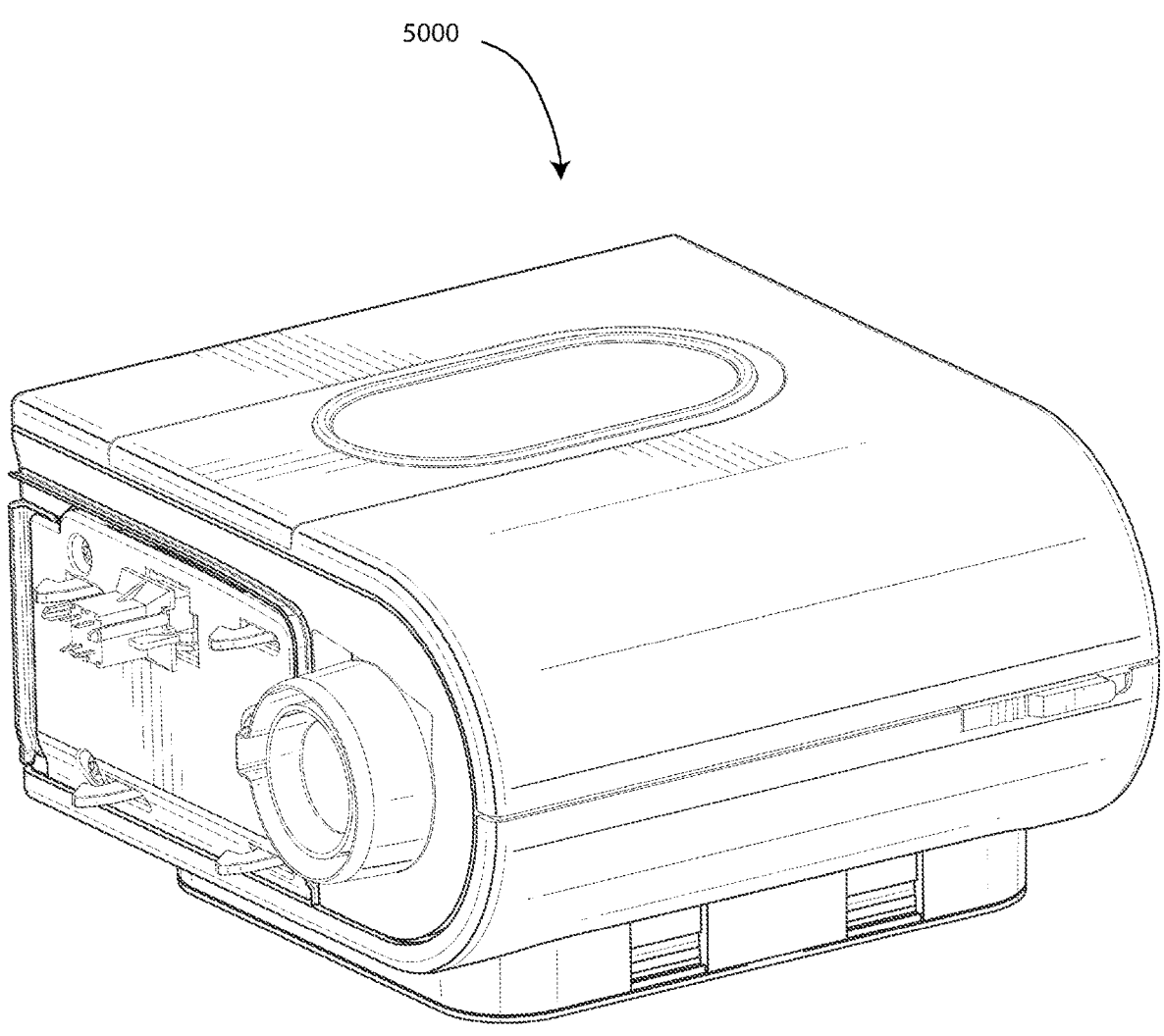

FIG. 5 shows an isometric view of a humidifier in accordance with one form of the present technology.

4.6 Breathing Waveforms

Figure 6A:
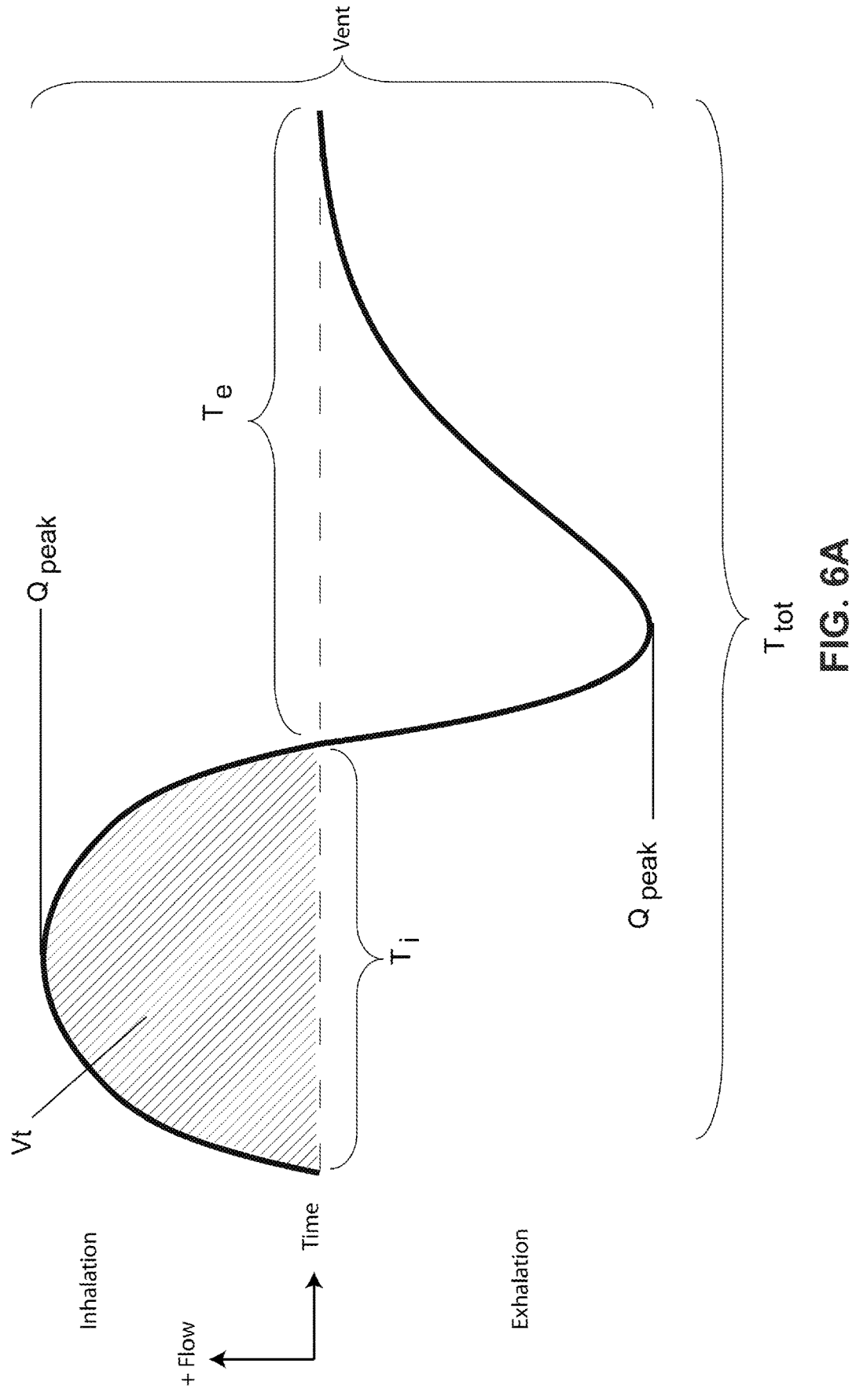

FIG. 6A shows a model typical breath waveform of a person while sleeping.

Figure 6B:
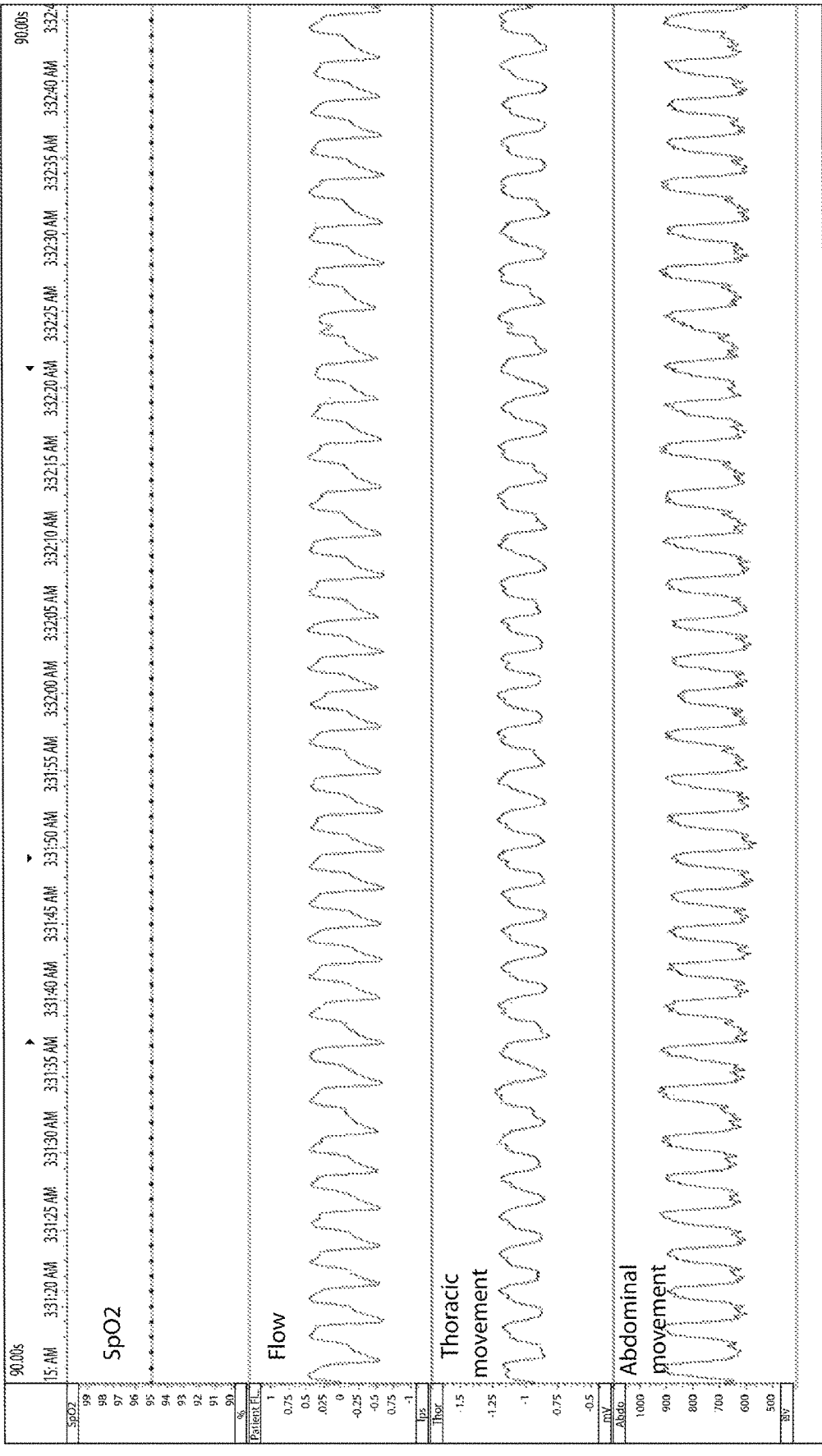

FIG. 6B shows polysomnography of a patient during non-REM sleep breathing normally over a period of about ninety seconds.

Figure 6C:
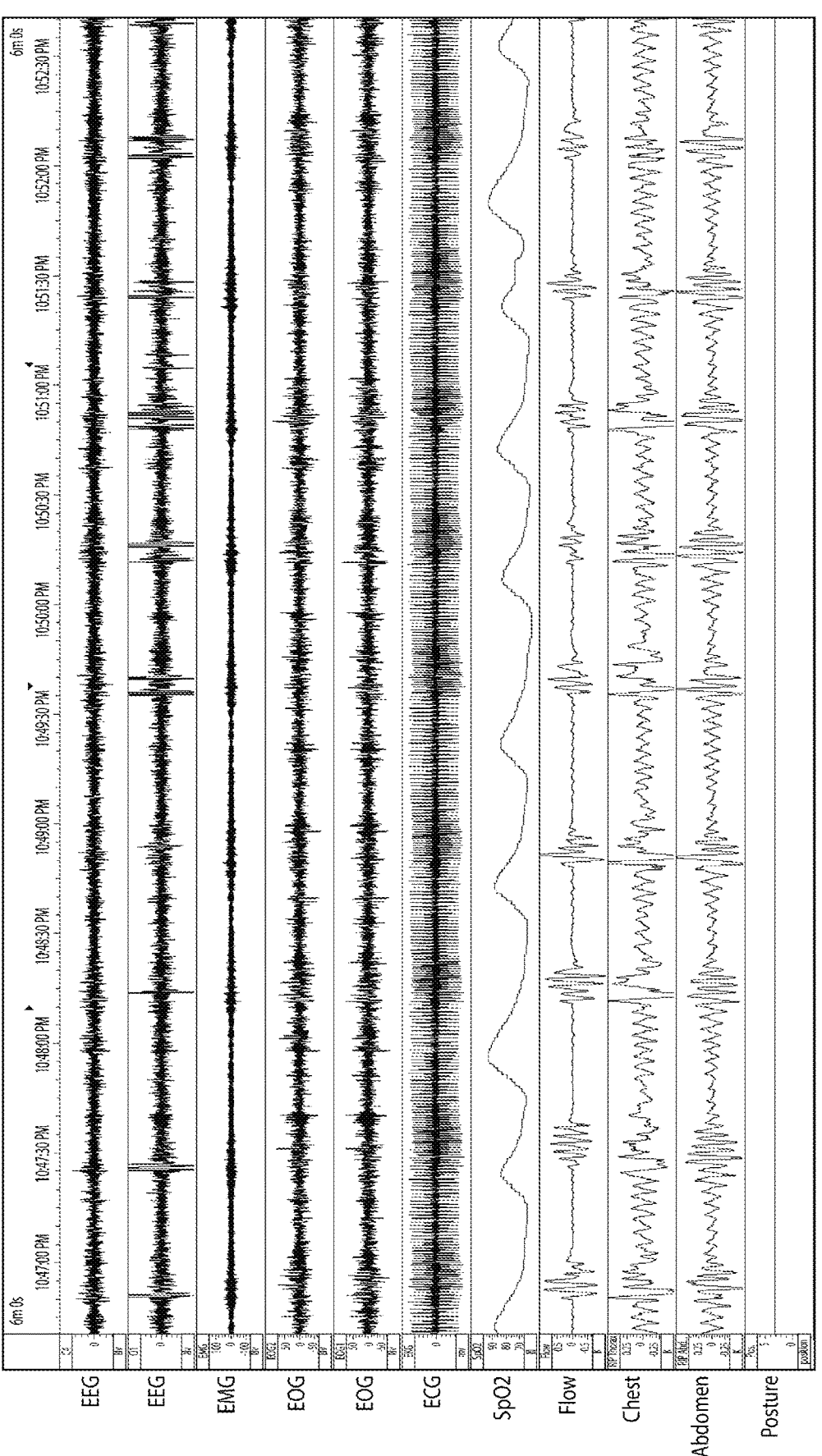

FIG. 6C shows polysomnography of a patient suffering from OSA without treatment over a period of about five minutes.

Figure 6D:
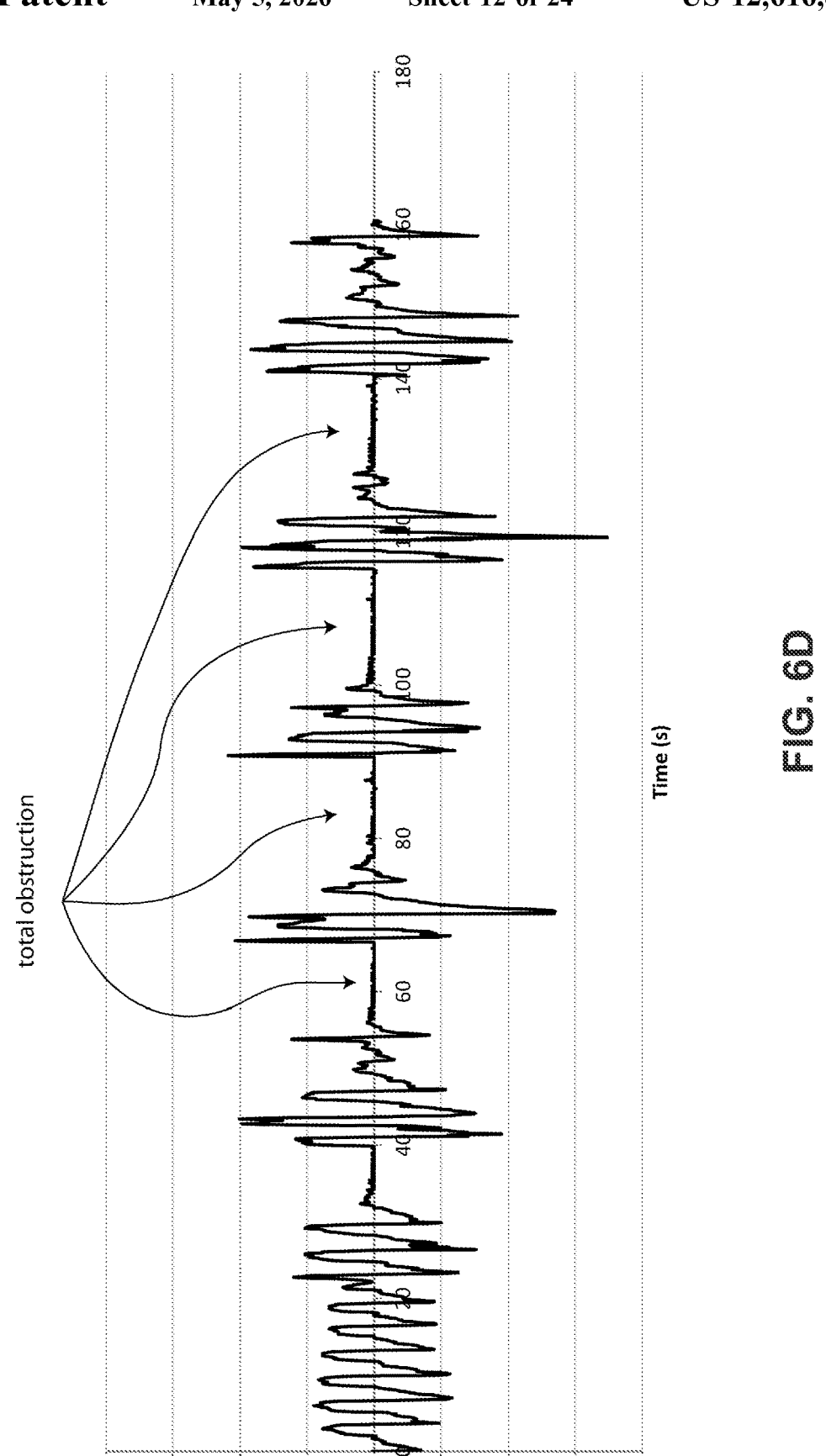

FIG. 6D shows a flow rate waveform of a patient experiencing a series of total obstructive apneas over a period of about three minutes.

4.7 Sleep Stage Inference

Figure 7A:
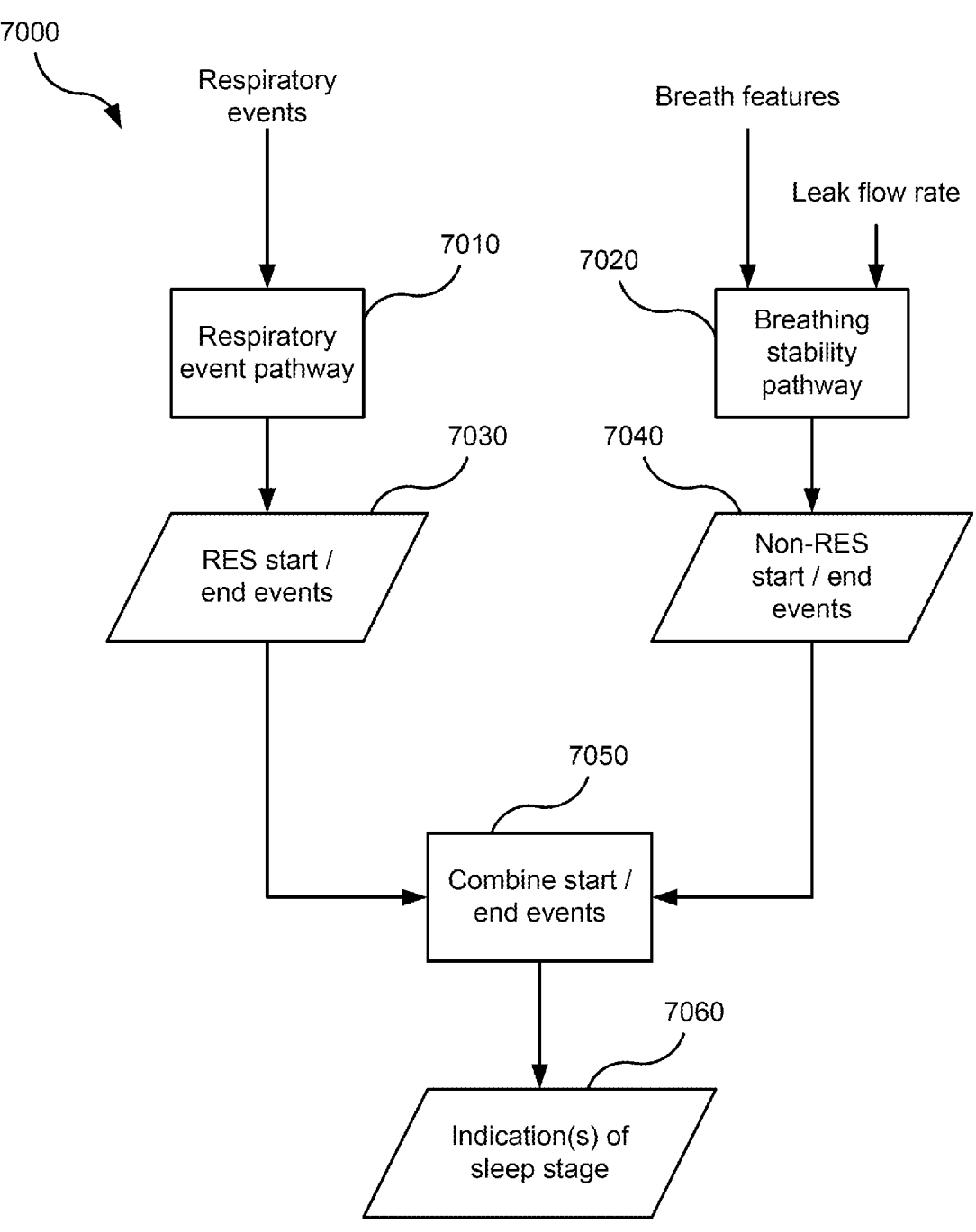

FIG. 7A is a flow chart illustrating a method that may be implemented to implement the sleep stage inference algorithm of FIG. 4D in one form of the present technology.

Figure 7B:
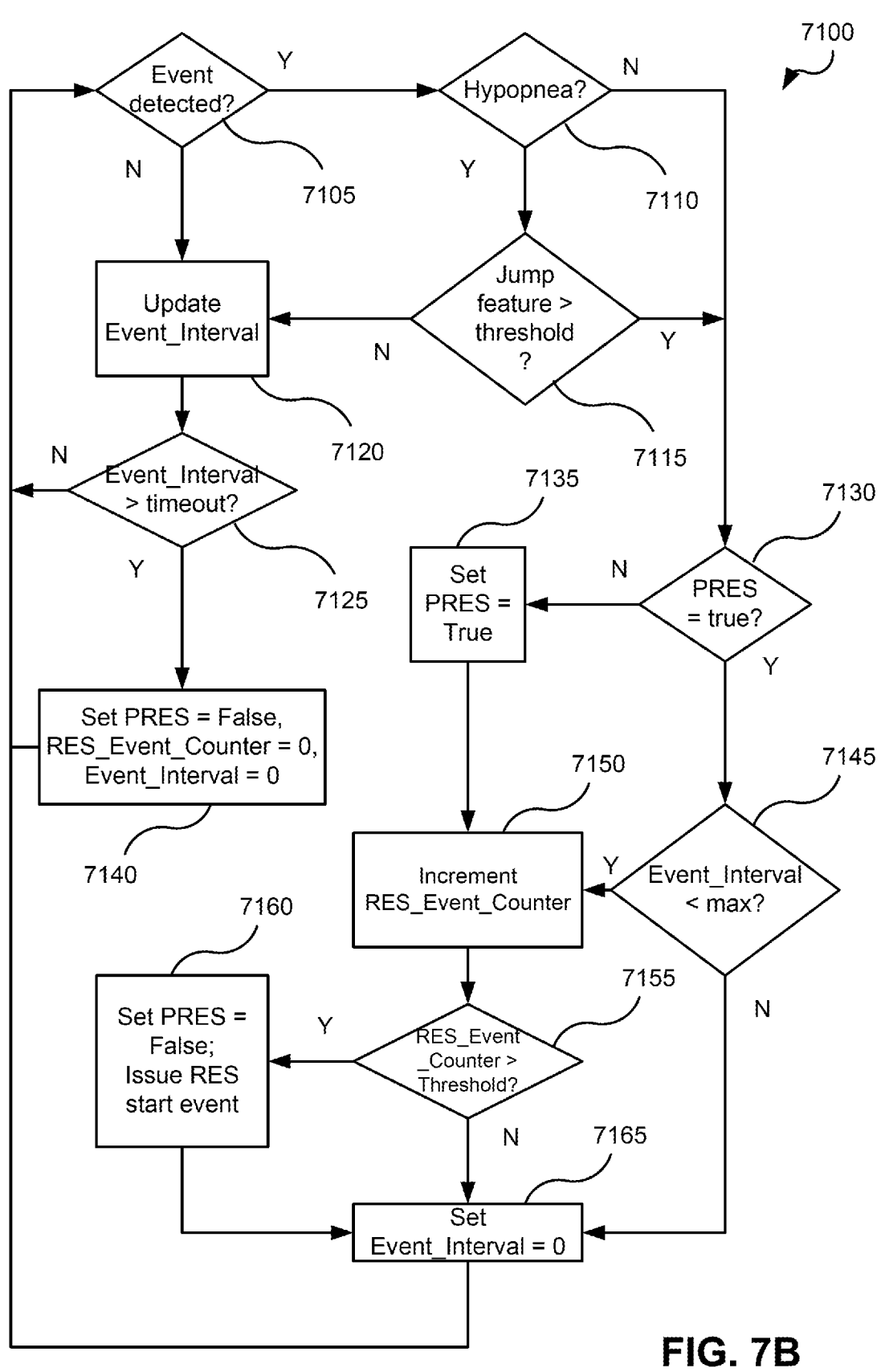

FIG. 7B is a flow chart illustrating a method that may be implemented to implement the respiratory event pathway of the method of FIG. 7A.

Figure 7C:

FIG. 7C is a flow chart illustrating a method that may be implemented to implement the breathing stability pathway of the method of FIG. 7A.

Figure 7D:
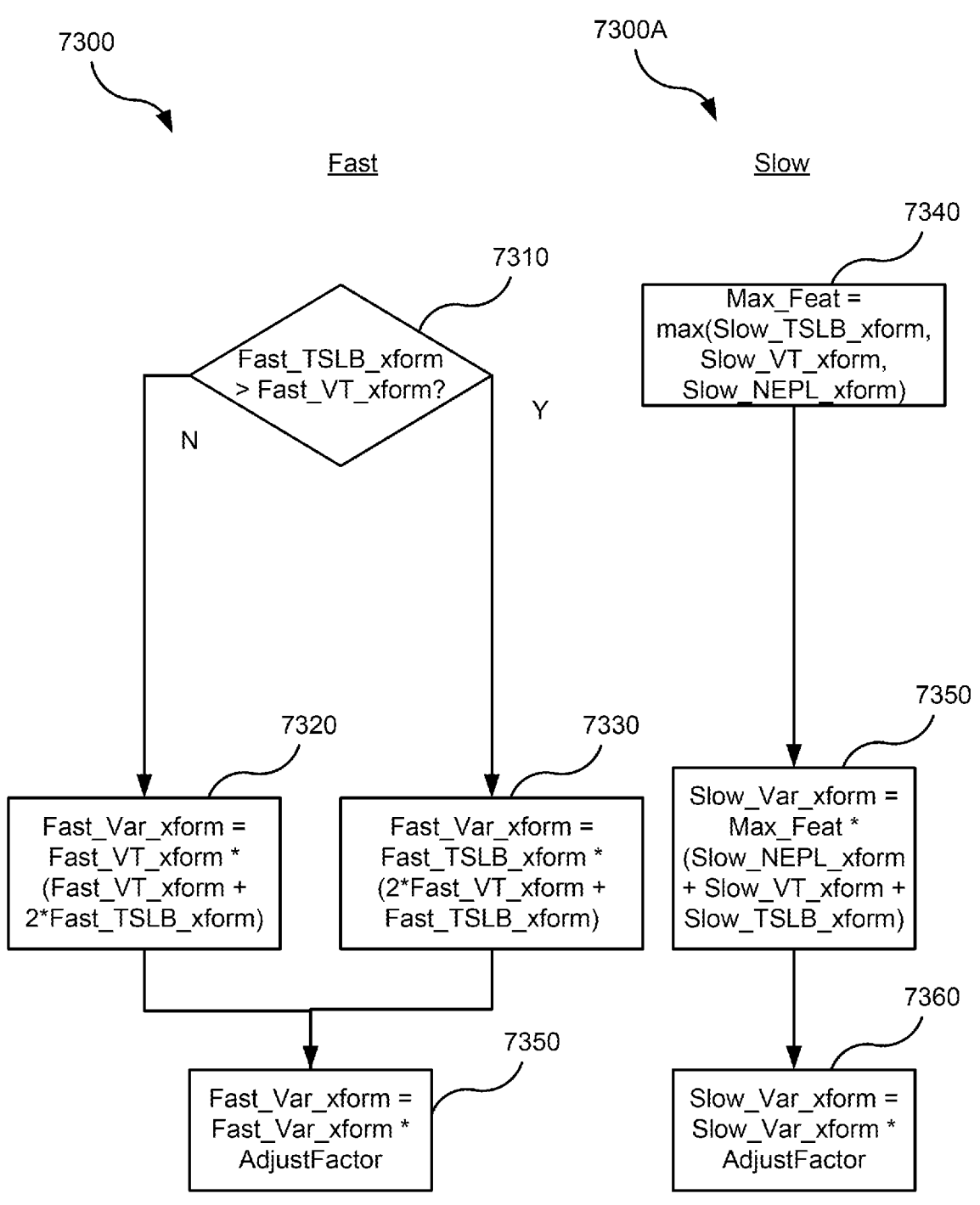

FIG. 7D is a flow chart illustrating methods that may be implemented for the feature combination step of the method of FIG. 7C for slow and fast timescales.

Figure 7E:
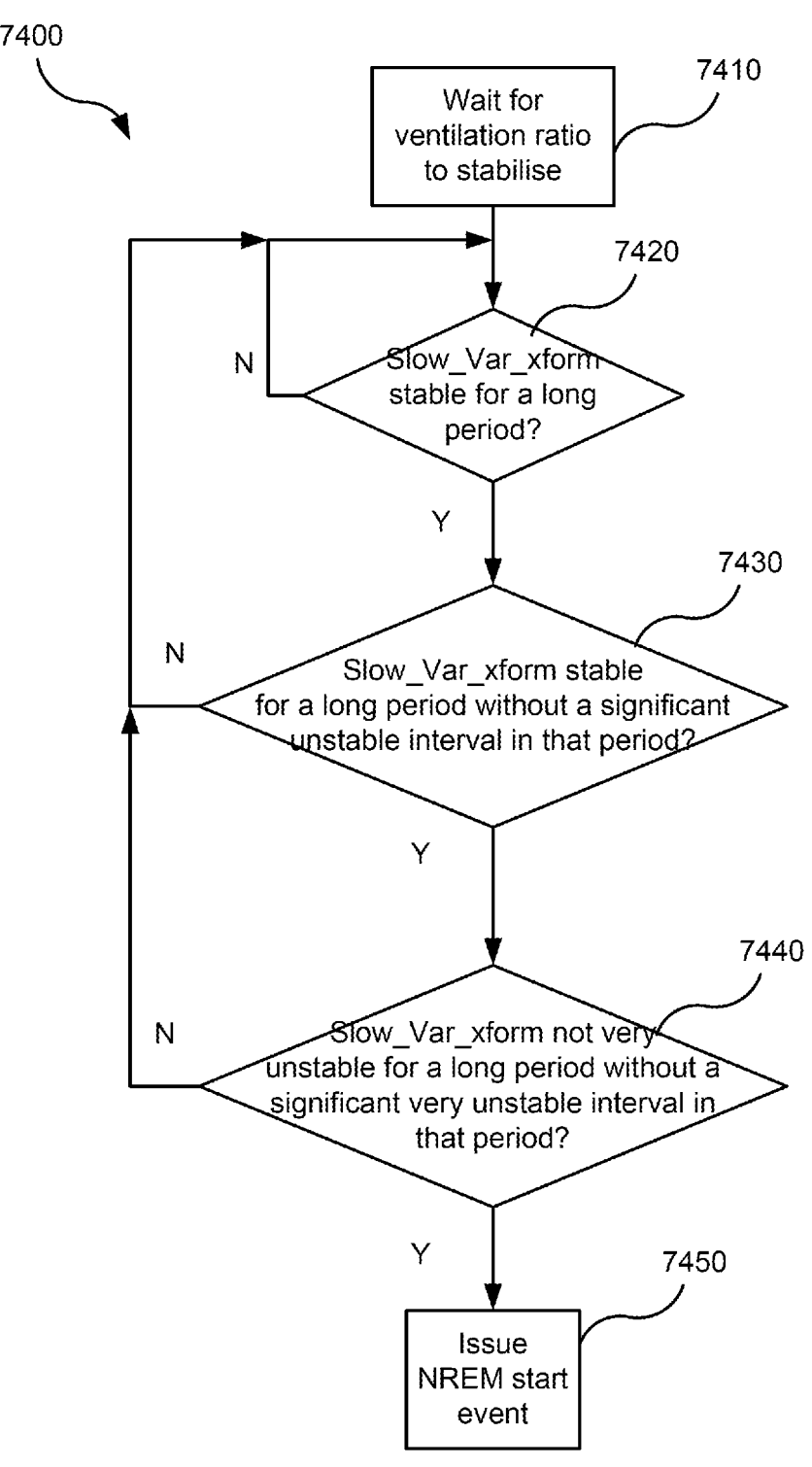

FIG. 7E is a flow chart illustrating a method that may be implemented to implement the sleep onset detector of FIG. 7C.

Figure 7F:
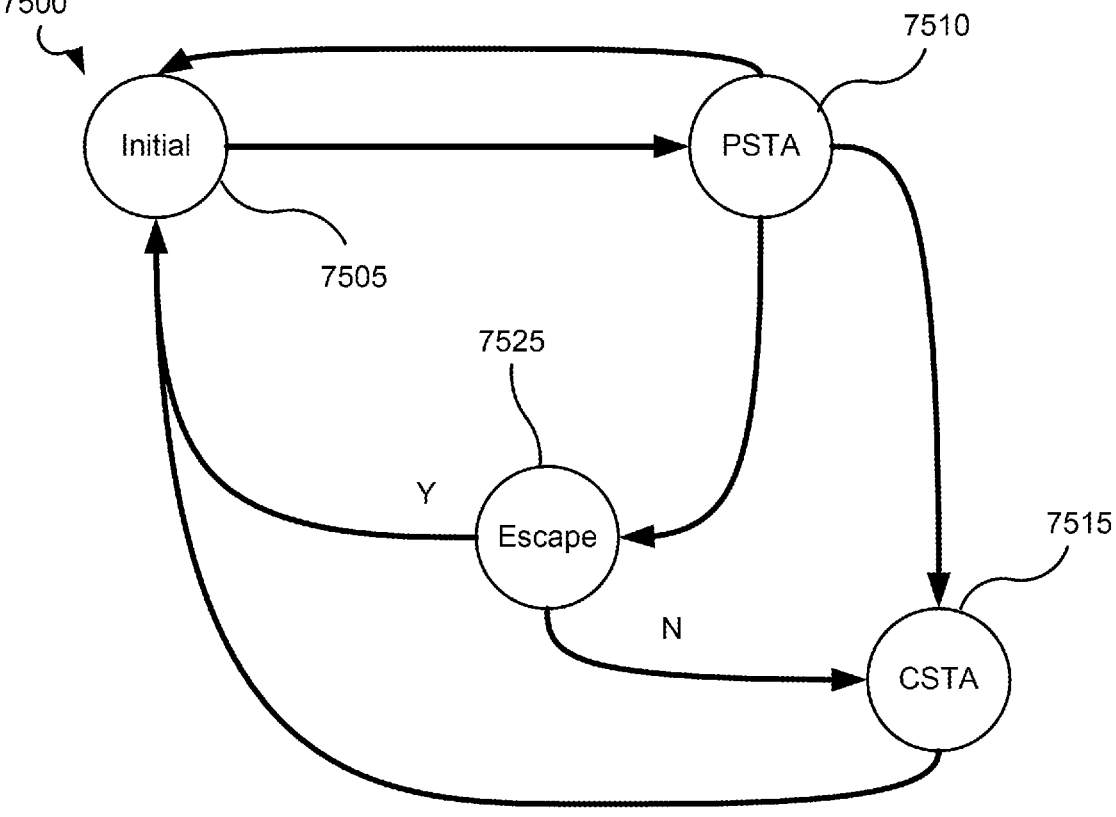

FIG. 7F is a state diagram illustrating a state machine that may implement the short-term awake pathway forming part of the wakefulness detector of FIG. 7C.

Figure 7G:
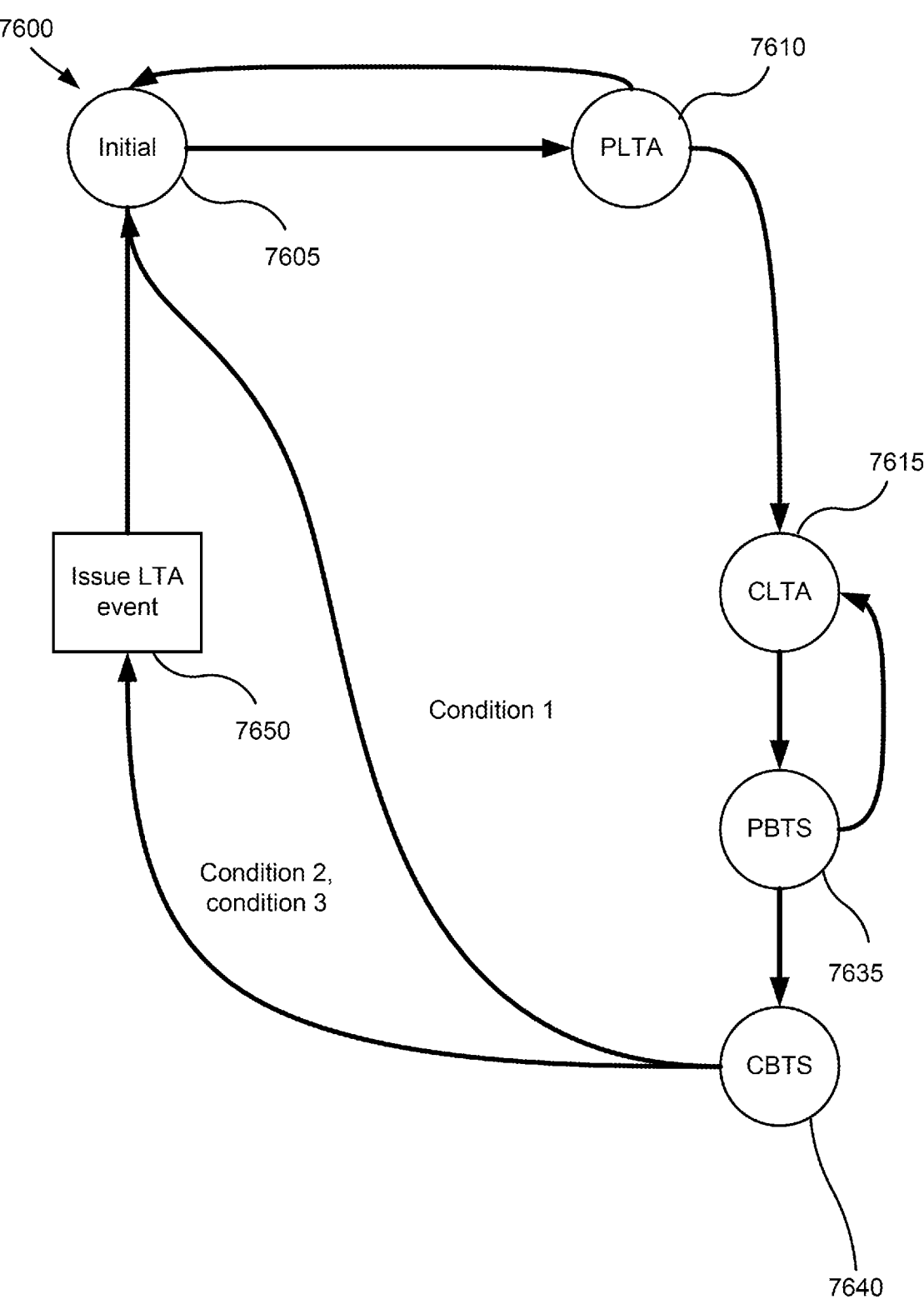

FIG. 7G is a state diagram illustrating a state machine that may implement the long-term awake pathway forming part of the wakefulness detector of FIG. 7C.

Figure 7H:
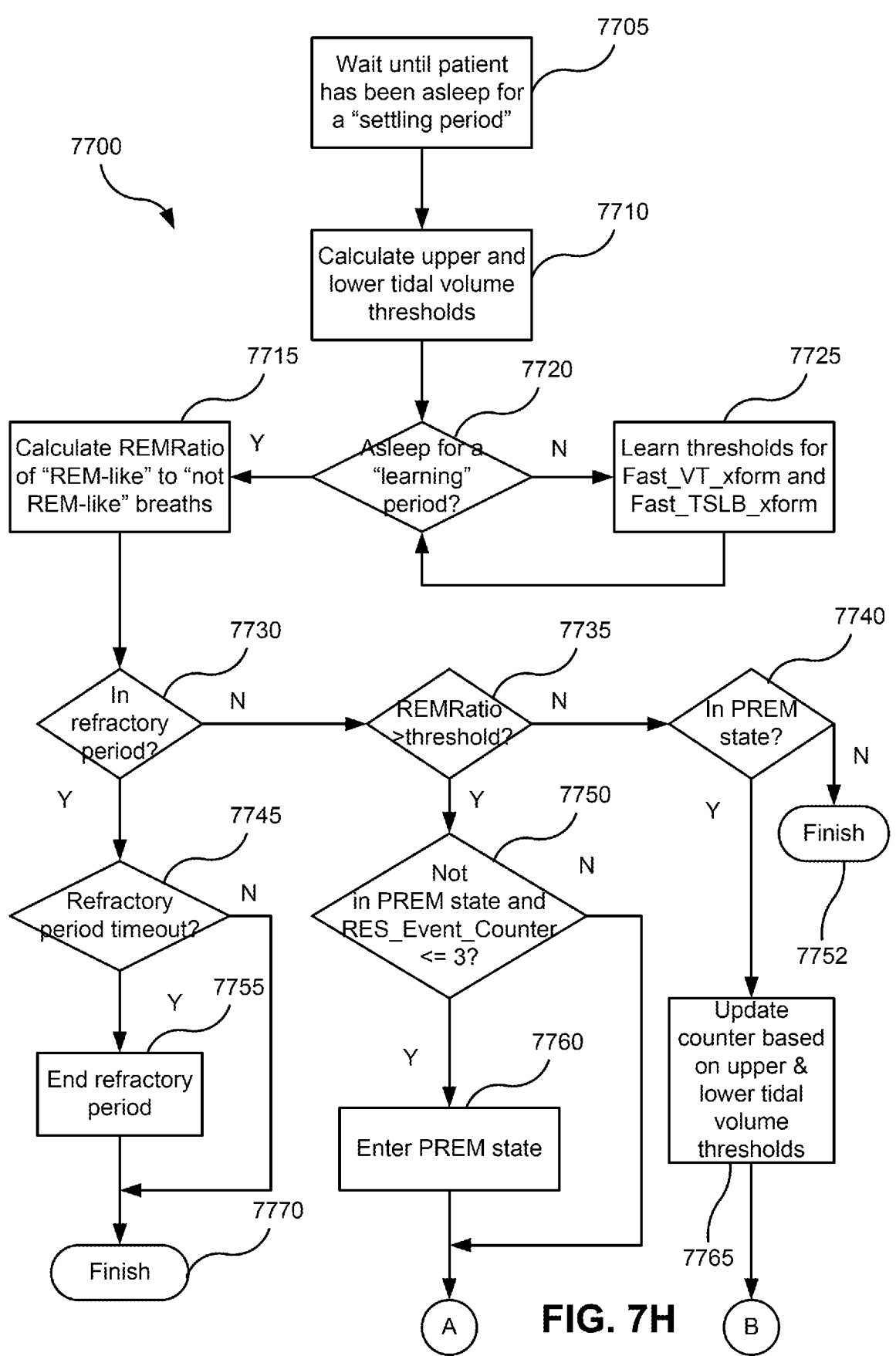
Figure 7I:
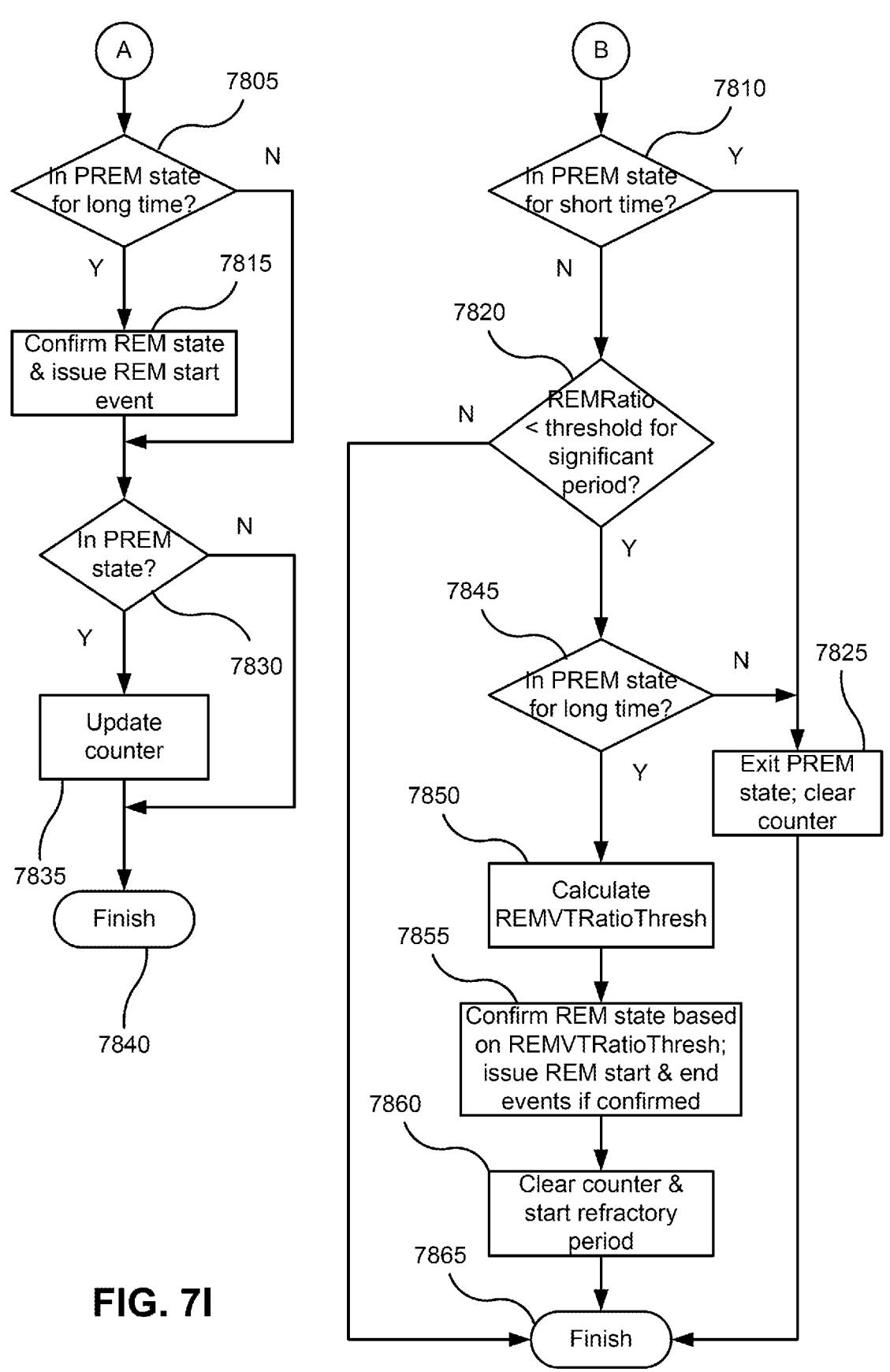

FIGS. 7H and 7I together contain a flow chart illustrating a method that may be implemented to implement the REM sleep detector of FIG. 7C.

Figure 7J:
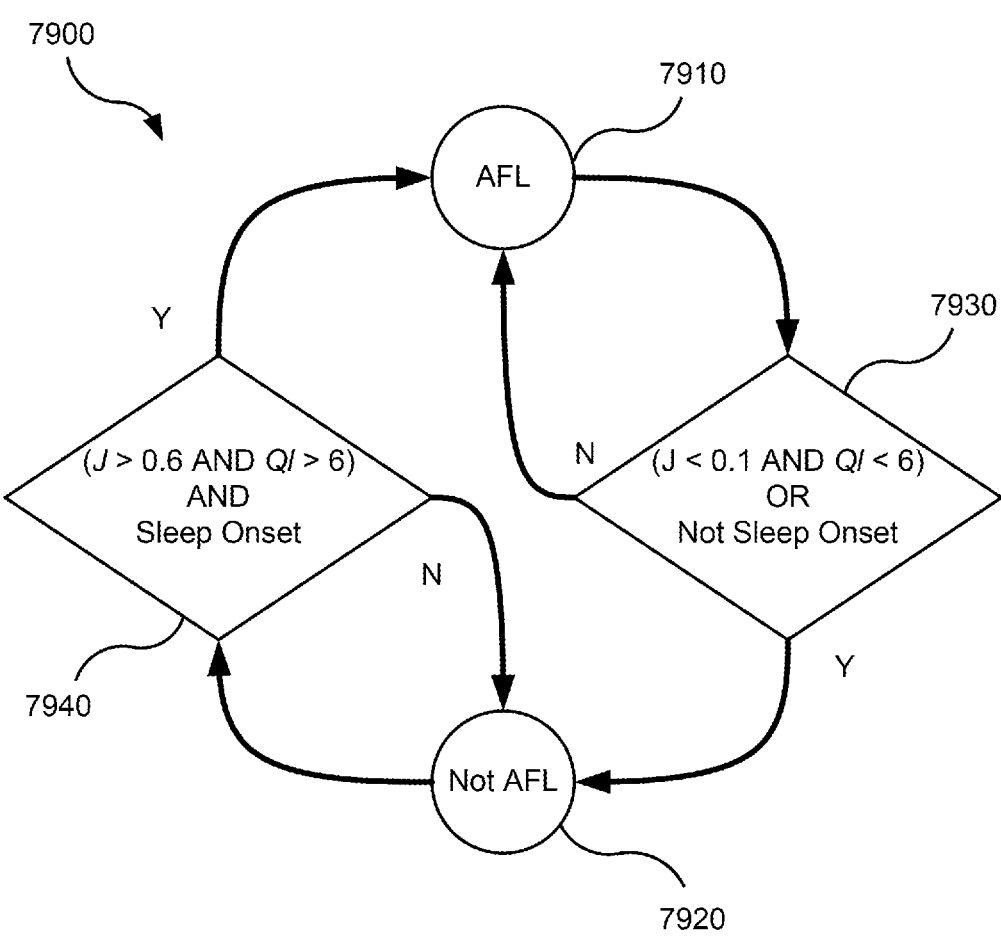

FIG. 7J is a state diagram illustrating a state machine that may implement part of the methods of FIG. 7D.

Figure 7K:
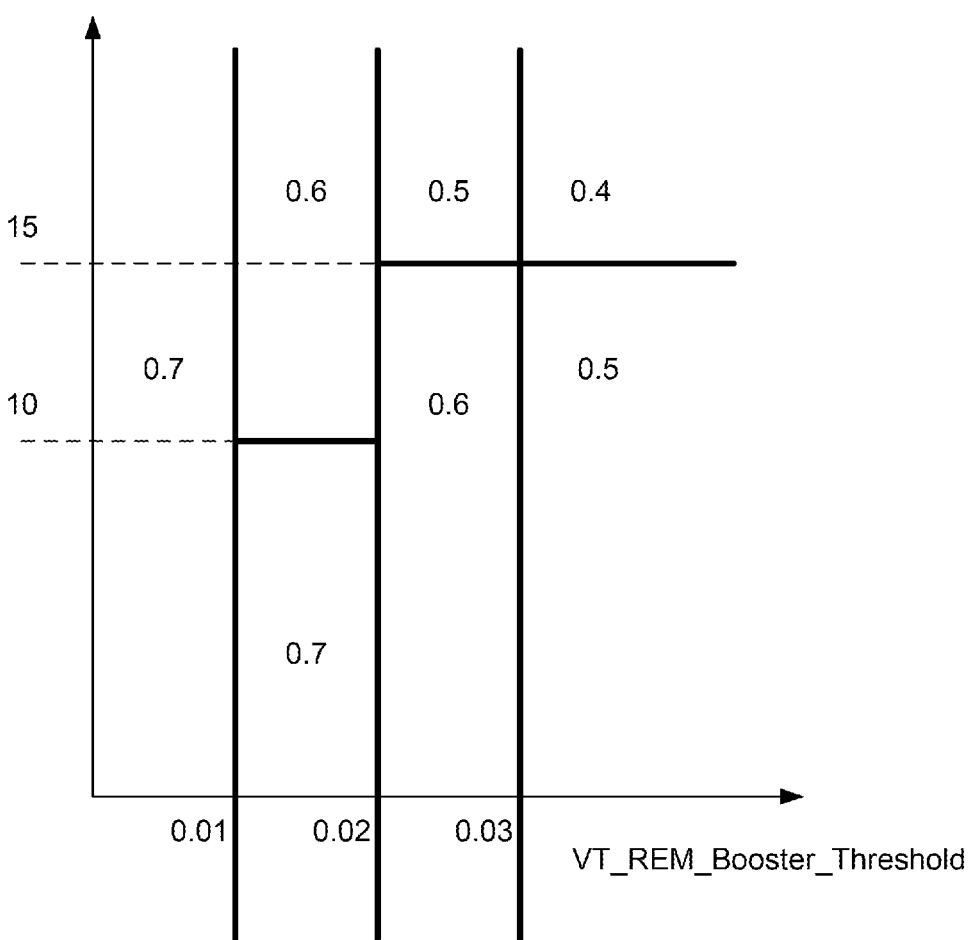
Figure 8:
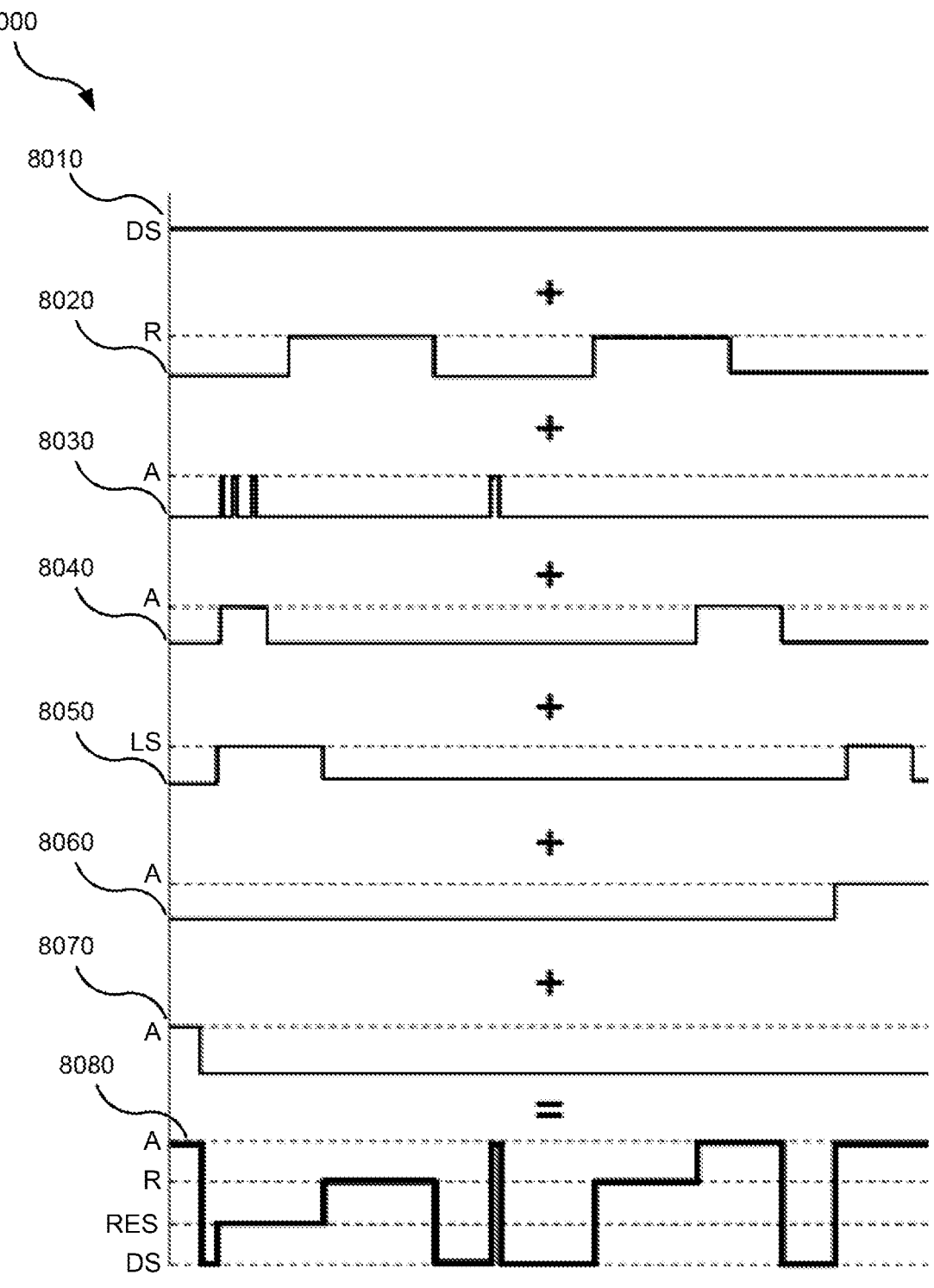

FIG. 7K is an illustration of an implementation of a step of the method of FIGS. 7H and 7I;

FIG. 8 contains an example graph illustrating the post-processing implementation of the event combination step of FIG. 7A.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of supplying a flow of air at positive pressure to the entrance of the airways of a patient 1000.

5.2 Treatment Systems

In one form, the present technology comprises an apparatus or device for treating a respiratory disorder. The apparatus or device may comprise an RPT device 4000 for supplying a flow of air at positive pressure to the patient 1000 via an air circuit 4170 to a patient interface 3000.

5.3 Patient Interface

A non-invasive patient interface 3000 in one form of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

5.4 RPT Device

An RPT device 4000 in one form of the present technology comprises mechanical and pneumatic components 4100, electrical components 4200 and is configured to execute one or more algorithms 4300. The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of delivering air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers housed in a volute. The blower may be capable of delivering a supply of air, for example at a rate of up to about 120 litres per minute, at a positive pressure in a range from about 4 $cmH_2O$ to about 20 $cmH_2O$, or in other forms up to about 30 $cmH_2O$. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to measure properties such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.4.1 Flow Rate Sensor

A flow rate sensor 4274 in accordance with the present technology may be based on a differential pressure transducer, for example, an SDP600 Series differential pressure transducer from SENSIRION.

In one form, a signal representing a flow rate from the flow rate sensor 4274 is received by the central controller 4230.

5.4.1.4.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal from the pressure sensor 4272 is received by the central controller 4230.

5.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall Effect sensor.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.1.6 Air Circuit

An air circuit 4170 in accordance with one form of the present technology is a conduit or a tube constructed and arranged to allow, in use, a flow of air to travel between two components such as the pneumatic block 4020 and the patient interface 3000.

In particular, the air circuit 4170 may be in fluid connection with the outlet of the pneumatic block and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

5.4.1.7 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.4.2 RPT Device Electrical Components 5.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.4.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may detect respiratory related events by analysis of stored data such as from any of the sensors described herein.

5.4.2.4 Clock

The RPT device 4000 may include a clock 4232 that is connected to the central controller 4230.

5.4.2.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

5.4.2.6 Protection Circuits

The one or more protection circuits 4250 in accordance with the present technology may comprise an electrical protection circuit, a temperature and/or pressure safety circuit.

5.4.2.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

5.4.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

5.4.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.2.9.1 Display Driver

A display driver 4292 receives as an input the characters, symbols, or images intended for display on the display 4294, and converts them to commands that cause the display 4294 to display those characters, symbols, or images.

5.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.4.3 RPT Device Algorithms

The algorithms 4300 in accordance with one form of the present technology comprise modules that, in general, receive as an input a signal from a transducer 4270, for example a flow rate sensor 4274 or pressure sensor 4272, and perform one or more process steps to calculate one or more output values. The output value(s) may in turn be used as input to another module, along with one or more transducer signal(s).

5.4.3.1 Pressure Compensation

In one form of the present technology, a pressure compensation algorithm 4312 receives as an input a signal indicative of the pressure in the pneumatic path proximal to an outlet of the pneumatic block. The pressure compensation algorithm 4312 estimates the pressure drop through the air circuit 4170 and provides as an output an estimated pressure, Pm, in the patient interface 3000.

5.4.3.2 Vent Flow Rate Estimation

In one form of the present technology, a vent flow rate estimation algorithm 4314 receives as an input an estimated pressure, Pm, in the patient interface 3000 and estimates a vent flow rate of air, Qv, from a vent 3400 in a patient interface 3000.

5.4.3.3 Leak Flow Rate Estimation

In one form of the present technology, a leak flow rate estimation algorithm 4316 receives as an input a total flow rate, Qt, and a vent flow rate Qv, and provides as an output an estimate of the leak flow rate Ql. In one form, the leak flow rate estimation algorithm estimates the leak flow rate Ql by calculating an average of the difference between total flow rate Qt and vent flow rate Qv over a period sufficiently long to include several breathing cycles, e.g. about 10 seconds.

In one form, the leak flow rate estimation algorithm 4316 receives as an input a total flow rate Qt, a vent flow rate Qv, and an estimated pressure, Pm, in the patient interface 3000, and provides as an output a leak flow rate Ql, by calculating a leak conductance, and determining a leak flow rate Ql to be a function of leak conductance and pressure, Pm. Leak conductance is calculated as the quotient of low pass filtered non-vent flow rate equal to the difference between total flow rate Qt and vent flow rate Qv, and low pass filtered square root of pressure Pm, where the low pass filter time constant has a value sufficiently long to include several breathing cycles, e.g. about 10 seconds. The leak flow rate Ql may be estimated as the product of leak conductance and a function of pressure, Pm.

5.4.3.4 Respiratory Flow Rate Estimation

In one form of the present technology, a respiratory flow rate estimation algorithm 4318 receives as an input a total flow rate, Qt, a vent flow rate, Qv, and a leak flow rate, Ql, and estimates a respiratory flow rate of air, Qr, to the patient, by subtracting the vent flow rate Qv and the leak flow rate Ql from the total flow rate Qt.

5.4.3.5 Breath Framing

In one form of the present technology, a breath framing algorithm 4321 receives an input a respiratory flow rate Qr, and returns a series of breaths, each breath being summarised by one or more breath features, e.g.:

Inspiratory time Ti and inspiratory tidal volume Vi

Expiratory time Te and expiratory tidal volume VE

Normalised expiratory peak flow rate location (NEPL)

Time since last breath (TSLB) (same as total time Ttot)

Conventional methods may be used to partition the respiratory flow rate waveform into breaths.

The NEPL may be computed from a breath by first locating the peak of expiratory flow rate relative to the start of expiration. The NEPL is then computed by dividing the expiratory peak flow rate location by the expiratory time Te. This value may be indicative of different sleep stages as follows:

(a) Awake: exhibits a large NEPL compared to sleep stages.

(b) REM Sleep: exhibits a small NEPL compared to wakefulness.

(c) non-REM Sleep: exhibits a small NEPL compared to wakefulness.

The breath framing algorithm 4321 may compute other breath features in addition to or instead of those listed above.

5.4.3.6 Ventilation Determination

In one form of the present technology, a ventilation determination algorithm 4322 receives an input a respiratory flow rate Qr, and determines a measure indicative of current patient ventilation, Vent. In one form, the ventilation determination algorithm 4322 determines the measure of current patient ventilation, Vent, as half the low-pass filtered absolute value of respiratory flow rate Qr. In one implementation, the low-pass filter has a time constant of three minutes.

In one form, the ventilation determination algorithm 4322 also computes a ventilation ratio VR that is a measure of a "big breath". Values of VR greater than 1 may be taken as indicating breaths that are large compared to the medium term ventilation. In one implementation, the ventilation determination algorithm 4322 computes the ventilation ratio VR as the mean inspiratory flow rate divided by the current ventilation, Vent. The mean inspiratory flow rate may be computed as the tidal volume $V_T$ (the average of inspiratory and expiratory tidal volumes $V_I$ and $V_E$ for the current breath) divided by the inspiratory time Ti.

5.4.3.7 Determination of Inspiratory Flow Limitation

In one form of the present technology, an inspiratory flow limitation determination algorithm 4323 receives as an input a respiratory flow rate signal Qr and provides as an output a metric of the extent to which the inspiratory portion of the breath exhibits inspiratory flow limitation. This measure is referred to as the flow limitation measure (FLM). In one such implementation, the computation of the flow limitation measure FLM is implemented as described in PCT Patent Publication no. WO 2008/138040, assigned to ResMed Ltd., the entire disclosure of which is hereby incorporated herein by cross-reference. This implementation produces a value of FLM in the range [0, 1], such that the closer the value of FLM is to 1, the more flow-limited is the inspiratory portion of the breath.

5.4.3.8 RERA Detection

In one form of the present technology, a RERA determination algorithm 4324 receives as an input a respiratory flow rate signal Qr and provides as an output a flag that indicates that a respiratory effort-related arousal (RERA) has been detected. In one form, the RERA detection algorithm 4324 receives as an input the current flow limitation measure FLM (from the inspiratory flow limitation determination algorithm 4323) and the current ventilation ratio VR (from the ventilation determination algorithm 4322) and provides as an output an indication of the occurrence of a RERA. Thus, a RERA may be detected based on one or more measures derived from sensor signals, such as a flow rate sensor or a respiration sensor. For example, the RERA indication may be determined based of a measure of SDB events and/or a measure of ventilation.

In one implementation, the RERA detection algorithm 4324 is based on the following methodology: if there has been elevated flow limitation recently (e.g., the flow limitation measure FLM is greater than a threshold, (e.g., 0)) followed by a step change in ventilation (indicating a sudden "big breath"), then a RERA is indicated.

To reduce the number of false positives, the RERA detection algorithm 4324 in some implementations evaluates recent consistency of elevated flow limitation, as well as a step change in ventilation indicating a sudden big breath.

In one such implementation, the detection of RERAs is implemented as described in PCT Patent Publication no. WO 2015/120522, assigned to ResMed Ltd., the entire disclosure of which is hereby incorporated herein by cross-reference.

5.4.3.9 Detection of Apneas and Hypopneas

In one form of the present technology, an apnea/hypopnea detection algorithm 4325 receives as an input a respiratory flow rate signal Qr and provides as an output a flag that indicates that an apnea or a hypopnea has been detected.

In one form, an apnea will be said to have been detected when a function of respiratory flow rate Qr falls below a flow rate threshold for a predetermined period of time. The function may determine a peak flow rate, a relatively short-term mean flow rate, or a flow rate intermediate of relatively short-term mean and peak flow rate, for example an RMS flow rate. The flow rate threshold may be a relatively long-term measure of flow rate.

In one form, a hypopnea will be said to have been detected when a function of respiratory flow rate Qr falls below a second flow rate threshold for a predetermined period of time. The function may determine a peak flow, a relatively short-term mean flow rate, or a flow rate intermediate of relatively short-term mean and peak flow rate, for example an RMS flow rate. The second flow rate threshold may be a relatively long-term measure of flow rate. The second flow rate threshold is greater than the flow rate threshold used to detect apneas.

5.4.3.10 Determination of Jamming

When the leak has recently changed and the leak flow rate estimation algorithm 4316 has not fully compensated for the change, a state designated as "jamming" exists. In one form of the present technology, a jamming determination algorithm 4326 receives as an input a respiratory flow rate signal Qr and provides as an output a jamming index J of the extent to which jamming is present.

In one form of the present technology, a jamming determination algorithm 4326 receives as an input the respiratory flow rate signal Qr and provides as an output the jamming index J.

In one implementation of the jamming determination algorithm 4326, the jamming index J is calculated as the fuzzy extent to which the absolute magnitude of the respiratory flow rate Qr has been large for longer than expected. The jamming index J may be determined according to the methods described in PCT Publication No. 2013/152403, the disclosure of which are incorporated herein by reference.

5.4.3.11 Determination of Airway Patency

In one form of the present technology, an airway patency determination algorithm 4327 receives as an input a respiratory flow rate signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 cmH$_2$O.

In one form, airway patency determination algorithm 4327 receives as an input a respiratory flow rate signal Qr, and determines the presence or absence of a cardiogenic signal. The absence of a cardiogenic signal is taken to be an indication of a closed airway.

5.4.3.12 Sleep Stage Inference

In one form of the present technology, a sleep stage inference algorithm 4328 receives as an input a respiratory flow rate signal Qr, and returns a time series of indications of a sleep stage being experienced by the patient 1000 at various times. The sleep stage inference algorithm 4328 is described in more detail below.

5.4.3.13 Determination of Therapy Parameters

In some forms of the present technology, the central controller 4230 executes one or more therapy parameter determination algorithms 4329 for the determination of one or more therapy parameters using the values returned by one or more of the other algorithms 4300. In one form of the present technology, the therapy parameter is an instantaneous treatment pressure Pt.

In some implementations of this form of the present technology, the treatment pressure Pt is identically equal to a base pressure Po throughout the respiratory cycle. Such implementations are generally grouped under the heading of CPAP therapy.

In CPAP therapy modes, the base pressure Po may be a constant value that is hard-coded or manually entered to the RPT device 4000. This alternative is sometimes referred to as constant CPAP therapy. Alternatively, the therapy parameter determination algorithm 4329 may repeatedly compute the base pressure Po during CPAP therapy. In this alternative, the therapy parameter determination algorithm 4329 repeatedly computes the base pressure Po as a function of indices or measures of sleep disordered breathing returned by the respective algorithms 4300, such as one or more of flow limitation, apnea, hypopnea, patency, and snore. This alternative is sometimes referred to as APAP therapy.

5.4.3.14 Therapy Control Module

The therapy control module 4330 in one form of the present technology receives as inputs the therapy parameters from the therapy parameter determination algorithm 4329, and controls the pressure generator 4140 to deliver a flow of air in accordance with the therapy parameters.

In one form of the present technology, the therapy parameter is a treatment pressure Pt, and the therapy control module 4330 controls the pressure generator 4140 to deliver a flow of air whose mask pressure Pm at the patient interface 3000 is equal to the treatment pressure Pt.

In other forms of the present technology, the therapy control module 4330 is inactive, so that the pressure generator 4140 does not deliver a flow of air to the patient, and the RPT device 4000 therefore acts purely as a monitoring device.

5.4.4 Sleep Stage Inference Algorithm

As mentioned above, in one form of the present technology, the central controller 4230 of the RPT device 4000 may include a sleep stage inference algorithm 4328, or a process to implement such an algorithm, to infer a sleep stage of the patient 1000.

In other forms of the present technology, the sleep stage inference algorithm 4328 may be implemented by a processor of the remote external device 4286, or remote external computing device, that is configured to communicate with the RPT device 4000 via the remote external communication network 4282. In such forms, the RPT device 4000 may send a signal representing the respiratory flow rate Qr to the remote external device 4286, or remote external computing device, via the remote external communication network 4282. The remote external device 4286 then implements the other algorithms 4300 to provide the necessary inputs for the sleep stage inference algorithm 4328.

In yet other forms, the sleep stage inference algorithm 4328 may be implemented partly by the central controller 4230 of the RPT device 4000, and partly by a processor of the remote external device 4286, or remote external computing device. For example, the central controller 4230 may process the respiratory flow rate signal to generate the start/end events described below, and transmit the events upon generation to the processor of the remote external device 4286, or remote external computing device, which may in turn process the events to generate the time series of indications of sleep stage inferred to have been experienced by the patient 1000 at corresponding time instants during the sleep session.

In any case, the sleep stage inference algorithm 4328 may operate in "real time", or as a post-process, that is, after the completion of the sleep session, on stored data representing the respiratory flow rate signal Qr over the sleep session. For post-processing implementations, the respiratory flow rate data may be stored as a time series of samples at a predefined sampling rate on the memory 4260 of the RPT device 4000, and/or on a memory of the remote external device 4286, or remote external computing device.

Again in any case, the sleep stage inference algorithm 4328 may operate independently of whether the RPT device 4000 actually delivers therapy to the patient 1000. That is, the sleep stage inference algorithm 4328 may still operate regardless of whether the therapy control module 4330 is active or inactive, i.e. whether the sleep session is a therapy session or a monitoring session.

In exclusive monitoring implementations (i.e., no simultaneous therapy) the RPT device 4000 may not even be present, and the central controller 4230, the memory 4260, and the transducers 4270 may instead reside in the patient interface 3000 or other device coupled with the patient interface 3000. In such implementations, the central controller 4230 may implement the sleep stage inference algorithm 4328 itself, or assist the processor of the remote external device 4286, or remote external computing device, to do so as described above.

In either real-time or post-processing implementations, the time series of indications of sleep stage may be stored in a hypnogram which may be saved to the memory of the implementing device for later access by other processes, such as AHI calculation as described above. In real-time implementations, the returned indications may be passed to the therapy control module 4330 and may be used thereby to influence therapy in ways described in more detail below.

FIG. 7A contains a flowchart illustrating a method 7000 that may be used to implement the sleep stage inference algorithm 4328. The method 7000 may be implemented by the central controller 4230 of the RPT device 4000 or a processor of the remote external device 4286, or remote external computing device, as described above.

The method 7000 employs two detection pathways, the "respiratory event" pathway 7010 and the "breathing stability" pathway 7020.

The breathing stability pathway 7020 is based on the observations that breathing instability is an indicator of wakefulness or rapid eye movement (REM) sleep and that breathing stability is an indicator of non-REM (NREM) sleep.

Breathing instability alone, however, is insufficient to infer sleep stage accurately, since whilst breathing instability is an indicator of wakefulness or REM sleep, it can also occur as a result of frequent respiratory events such as apneas, hypopneas, and RERAs, which occur during sleep. It is therefore helpful to distinguish periods of breathing instability that are largely driven by respiratory events from periods of genuine wakefulness. Respiratory events are indicators of respiratory event sleep (RES). The respiratory event pathway 7010 may therefore analyse respiratory events returned by the algorithms 4324 (RERA) and 4325 (Apnea/Hypopnea) and generate RES start/end events 7030 indicating the start and end times of episodes of RES.

The breathing stability pathway 7020 analyses the breath features returned by the breath framing algorithm 4321, along with the leak flow rate Ql estimated by the leak flow rate estimation algorithm 4316, and generates non-RES start/end events 7040 indicating the start and end times of episodes of non-RES, i.e. sleep that is not respiratory event sleep (REM or NREM).

The RES and non-RES start/end events 7030 and 7040 each have a priority that is derived from the pathway from which they were generated. The RES and non-RES start/end events 7030 and 7040 are combined at step 7050 based on their respective priorities to produce an indication, or indications, 7060 of a sleep stage of the patient. The indication takes one of four values indicating one of the following four sleep stages:

a. Wakefulness
b. Non-REM (NREM) (deep) sleep
c. REM sleep
d. Respiratory event sleep (RES)

The detection pathways 7010 and 7020 may be said to operate in parallel. In this regard, the discrete logic of the process of a detection pathway may have an apparent or actual simultaneous performance (e.g., parallel computing, parallel processing, multithreading, etc.) with the discrete logic of the process of the other detection pathway.

Steps 7010, 7020, and 7050 of the method 7000 are described in more detail below.

5.4.4.1 Respiratory Event Pathway

The respiratory event pathway 7010 looks for a series of respiratory events in close succession before generating a RES start event. Once the respiratory events thin out (e.g., reduce in frequency), the respiratory event pathway 7010 generates a RES end event.

FIG. 7B is a flow chart illustrating a method 7100 that may be used to implement the respiratory event pathway 7010. The method 7100 starts at step 7105, which checks whether a respiratory event (apnea, hypopnea, or RERA) has been detected by the apnea/hypopnea detection algorithm 4325 or the RERA detection algorithm 4324. If not ("N"), step 7120 updates the timer variable Event Interval, which measures the time since the last respiratory event. Step 7125 then determines whether Event Interval exceeds a timeout threshold, set in one implementation to 5 minutes but in other implementations to between 1 and 30 minutes. If not ("N"), the method 7100 returns to step 7105. If so ("Y"), the method 7100 at step 7140 sets a Boolean variable PRES (indicating the respiratory event pathway 7010 is in a provisional RES state) to False, and sets the Event Interval timer and a respiratory event counter RES_Event_Counter representing the number of respiratory events in the series to zero. Step 7140 also issues a RES end event equal to the current time if the last event issued was a RES start event (step 7160). The method 7100 then returns to step 7105.

If a respiratory event was detected at step 7105 ("Y"), step 7110 determines whether the event was a hypopnea. If so ("Y"), step 7115 determines whether the jump feature for the hypopnea exceeds a threshold, set in one implementation to 0.5, indicating the hypopnea was obstructive. The jump feature, which is a measure of how quickly the patient's breathing recovers from the hypopnea, may be computed as described in, for example, PCT publication no. WO 2006/066337, titled "Method for detecting and discriminating breathing patterns from respiratory signals", the entire contents of which are incorporated herein by reference.

If the hypopnea was not obstructive ("N"), the method 7100 proceeds to step 7120, since non-obstructive hypopneas are not useful in determining sleep stage. Otherwise ("Y"), the method 7100 proceeds to step 7130. If the detected event from step 7105 was not a hypopnea ("N"), the method 7000 proceeds directly to step 7130. Step 7130 determines whether the Boolean variable PRES is True, indicating the respiratory event pathway is in a provisional RES state. If not ("N"), step 7135 sets PRES to True. Step 7150 then increments the event counter RES_Event_Counter. Otherwise ("Y"), step 7145 checks whether the timer Event Interval is less than a value "max", set in one embodiment to 3 minutes, representing the maximum interval between respiratory events to be regarded as part of a series. If so ("Y"), step 7150 follows. Otherwise ("N"), the method 7100 sets the timer Event Interval to zero at step 7165, and returns to step 7105 to await another respiratory event.

Step 7150 increments the counter RES_Event_Counter. At step 7155, which follows step 7150, the method 7100 determines whether the counter RES_Event_Counter exceeds a threshold representing the minimum number of respiratory events in a series indicative of RES. In one implementation, the threshold is set to 5, though in other implementations threshold values from 3 to 15 may be used. If not ("N"), step 7165 follows as described above. Otherwise ("Y"), step 7160 confirms the start of respiratory event sleep by setting the Boolean variable PRES to False and issuing a RES start event indicating the time at which PRES was last set to TRUE in step 7135. Step 7165 then follows as described above.

An alternative implementation of the respiratory event pathway 7010 uses a variant of the method 7100 that handles respiratory events slightly differently. Each detected respiratory event is either high or low confidence. The following events are defined as high confidence events:

Apneas (whether obstructive or central)

Obstructive hypopneas

RERA s

The following events are defined as low confidence events:

Non-obstructive hypopneas

Under the alternative implementation, step 7115, instead of proceeding to step 7120 in the event of a "N", proceeds to step 7130 knowing that the detected event is a low confidence event. High confidence events increment the RES event counter (step 7150) by 3 and low confidence events increment the RES event counter by 1. Step 7155, in addition to checking whether the RES event counter exceeds a threshold, checks whether the current series of respiratory events contains at least 1 high confidence event, and whether a ratio TSLB_10_Breath_Diff_Ratio derived from the difference feature TSLB_10_Breath_Diff (see below) is less than a threshold (e.g. 0.4). The ratio TSLB_10_Breath_Diff_Ratio may be computed as a ratio of the number of times the updated value of TSLB_10_Breath_Diff falls below a threshold (e.g. 0.5) to the total number of updates.

5.4.4.2 Breathing Stability Pathway

A patient's breathing will differ depending on which sleep stage they are in. Whilst awake, the breathing may vary significantly and during deep (NREM) sleep there may be very little variation. REM sleep presents a challenge in that breathing also varies in this sleep stage, but the extent of variability is not consistent on a night to night basis. Regardless, the variability of breath features offers insight to help discriminate between sleep stages. The breathing stability pathway 7020 therefore first computes the variability of breath features, then uses the variability to infer sleep stage.

Given that sleep stage can change as sharply as arousals lasting 30 seconds, and as gradually as awakenings exceeding 60 minutes in duration, it is important that analysis is done with respect to different timescales. In one implementation of the breathing stability pathway 7020, variability of breath features is computed over two different timescales:

Slow timescale (e.g. 30 breaths, 5 breaths, or 150 breaths, or defined in time terms e.g. 30 seconds, 600 seconds, 1 hour)

Fast timescale (a small fraction, e.g. ⅙, of the slow timescale)

In one implementation, variability of breath features over each timescale is quantified as their statistical variance. The raw variances of the breath features are then transformed to a uniform discrete numeric scale. This transformation permits comparing and combining operations to be performed "fairly" on variances of different breath features. Following transformation, the discrete numerical values are combined into one consolidated variance feature for each timescale. Various sleep stage detectors (e.g., sleep onset, REM sleep, and various forms of wakefulness) then operate on the consolidated variance features, plus some other derived features to be described below.

FIG. 7C is a flow chart illustrating a method 7200 that may be used to implement the breathing stability pathway in some forms of the present technology. The method 7200 starts at step 7210, which calculates the variances over the "slow" and "fast" timescales mentioned above of one or more breath features calculated by the breath framing algorithm 4321. In one implementation, the following breath features are used:

tidal volume $V_T$

Normalised expiratory peak flow rate location (NEPL)

Time since last breath (TSLB)

The result is six breath "variance features", one at each timescale for each breath feature. In other implementations other breath features may be used, e.g. breathing rate, inspiratory/expiratory peak flow rates, breathwise ventilation, etc.

Step 7220 then transforms the variance features at each timescale to a uniform discrete numeric scale. In one implementation, the discrete numeric scale is the integers 0 to 4, and step 7220 makes the transformations according to a set of thresholds T1 to T4, such that the transformed discrete value is 4-n if the variance feature is between threshold $T_n$ and threshold $T_{n+1}$. (T0 is identically zero and T5 is infinity.) In this manner, the highest transformed value corresponds to the lowest variance, so the transformed feature is a measure of stability of the corresponding breath feature.

In one such implementation, the thresholds T1 to T4 for each variance feature are shown in the following table:

| Variance feature | T1 | T2 | T3 | T4 |
|---|---|---|---|---|
| $V_T$ (fast) (ml$^2$) | 750 | 1500 | 3000 | 3000 |
| $V_T$ (slow) (ml$^2$) | 750 | 2000 | 5000 | 15000 |
| TSLB (fast) (sec$^2$) | 0.15 | 0.3 | 0.7 | 1 |
| TSLB (slow) (sec$^2$) | 0.15 | 0.3 | 0.7 | 1 |
| NEPL (fast) | 0.0007 | 0.0015 | 0.005 | 0.01 |
| NEPL (slow) | 0.0007 | 0.0015 | 0.005 | 0.01 |

Following transformation at step 7220, step 7225 combines the transformed variance features at each timescale into a single consolidated variance feature for the timescale, yielding two consolidated variance features, referred to as Slow_Var_xform and Fast_Var_xform for the slow and fast timescales respectively.

FIG. 7D is a flow chart illustrating methods 7300 and 7300A that may be used to implement the combination step 7225 for each timescale in one implementation. For the slow timescale, the method 7300A uses the transformed values of the slow timescale breath variance features and the result is the slow consolidated variance feature Slow_Var_xform. For the fast timescale, the method 7300 uses the transformed values of the fast timescale breath variance features and the result is the fast consolidated variance feature Fast_Var_xform.

In the method 7300 for the fast timescale, the first step 7310 determines whether the transformed fast TSLB value is greater than the transformed fast tidal volume value. If so ("Y"), step 7330 computes the fast consolidated variance feature Fast_Var_xform as follows:

Fast_Var_xform=Fast_TSLB_xform*(2*Fast_VT_xform+Fast_TSLB_xform)

If not ("N"), step 7320 computes the fast consolidated variance feature Fast_Var_xform as follows:

Fast_Var_xform=Fast_VT_xform*(Fast_VT_xform+2*Fast_TSLB_xform)

In the method 7300A for the slow time scale, the first step 7340 determines the maximum Max_Feat of the three transformed values Slow_TSLB_xform, Slow_VT_xform, and Slow_NEPL_xform. Step 7350 then computes the consolidated variance feature Slow_Var_xform as follows:

Slow_Var_xform=Max_Feat*(Slow_NEPL_xform+Slow_VT_xform+Slow_TSLB_xform)

The resulting consolidated variance features Slow_Var_xform and Fast_Var_xform are integer-valued between 0 and 48, with high values indicating stability of breath features and low values indicating instability over their respective timescales.

Steps 7350 and 7360 then adjust the fast and slow consolidated variance features respectively for the presence of leak by multiplying them by a leak adjustment factor AdjustFactor. The value of the leak adjustment factor AdjustFactor depends on whether the system is in an 'Adjust for Leak' state.

FIG. 7J is a state diagram illustrating a state machine 7900 that may be used to determine the 'Adjust for Leak' state used by the methods 7300 and 7300A to compute the leak adjustment factor AdjustFactor. The state machine 7900 operates as follows. While in state 7910 (Adjust for leak or AFL), the conditions at 7930 are checked. If not satisfied ("N"), the state machine 7900 remains in the AFL state 7910. If satisfied ("Y"), the state machine 7900 transitions to the Not AFL state 7920. The conditions of 7930 are that the jamming index J is less than a threshold (e.g. 0.1) and the average leak flow rate Ql is less than a threshold (e.g. 6 litres per minute), or the system is not in the non-REM state (as described below in relation to sleep onset detection).

While the state machine 7900 is in the Not AFL state 7920, the conditions at 7940 are checked. If not satisfied ("N"), the state machine 7900 remains in the Not AFL state 7920. If satisfied ("Y"), the state machine 7900 transitions to the AFL state 7910. The conditions of 7940 are that the jamming index J is greater than a threshold (e.g. 0.6) and the average leak flow rate Ql is greater than a threshold (e.g. 6 litres per minute), and the system is in the non-REM state.

In the Not AFL state, the leak adjustment factor AdjustFactor is equal to one.

In the AFL state, the leak adjustment factor AdjustFactor is computed as per the following equation:

$$AdjustFactor = \begin{cases} 0, & \text{if } Ql < 6lpm \\ \dfrac{Ql-6}{18}, & \text{if } 6 \le Ql < 24lpm \\ 1, & \text{if } Ql \ge 24lpm \end{cases}$$

Returning to the method 7200, step 7230 calculates various difference features from the breath features. Difference features are calculated to act as conditioning features for REM/Awake state transitions. Whilst variance features are very insightful, one of their major drawbacks is that they can at times be oversensitive (even using the slow timescale variance features). Difference features are similar to variance features, but they are calculated in such a way that they reflect only gross changes between two sections of breathing. As a result, they are not as sensitive and can be used as conditioning features.

The following difference features are calculated as the root mean squared difference between features of corresponding breaths over two consecutive ten-breath sections of breathing:

VT_10_Breath_Diff (based on tidal volume $V_T$)

TSLB_10_Breath_Diff (based on TSLB)

Step 7240 of the method 7200 calculates two trend features representing the "natural" or "typical" value of tidal volume $V_T$ over long and short timescales respectively:

Long_Term_VT_Trend

Short_Term_VT_Trend

The trend features are calculated by maintaining a rolling histogram of tidal volume $V_T$ over each timescale and extracting a measure of central tendency from each histogram using a conventional statistical technique, e.g. mean, median, mode, etc. after each update to the histogram.

Long_Term_VT_Trend is updated at all times when the Slow_Var_xform is greater than a threshold (eg. 20) and leak flow rate Ql is below a threshold (eg. 3 litres per minute). The only exception is during provisional awake states (see below), where Long_Term_VT_Trend is not updated. Short-_Term_VT_Trend is updated only during provisional awake states.

Difference, trend, and consolidated variance features calculated at steps 7230, 7240, and 7225 are placed into histograms in order to calculate thresholds required for the subsequent modules. Step 7250 calculates the thresholds as representative values of the respective histograms. In one implementation, a representative value may be the relative power of the two largest bins of the histogram. The thresholds and their respective histograms are as follows:

VT_REM_Booster_Threshold

This threshold is calculated based on a histogram of VT_10_Breath_Diff values.

TSLB Awake Threshold

This threshold is calculated based on a histogram of TSLB_10_Breath_Diff values.

Slow_Var_xform_Threshold_Filtered

This threshold is only calculated after the first fifteen minutes after sleep onset, based on a histogram of Slow_Var_Transform values.

Slow_Var_xform_Threshold_Complete

This threshold is calculated based on a histogram of Slow_Var_Transform values.

Long_Term_VT_Trend Threshold

This threshold is calculated based on a histogram of tidal volume values $V_T$.

Short_Term_VT_Trend Threshold

This threshold is only calculated during provisional awake states based on a histogram of tidal volume values $V_T$.

The method 7200 then uses the variance, trend, and difference features and thresholds calculated at steps 7210 to 7250 in three detectors: a sleep onset detector 7260, a REM sleep detector 7270, and a wakefulness detector 7280. Each detector issues start/end events, i.e. times of start/end of its associated sleep stage, as soon as the detector confirms that the associated stage has started/ended (there may be a significant delay between the actual start/end time of the stage and the confirmation that it has occurred). The sleep onset detector 7260 issues NREM start events; the REM sleep detector 7270 issues REM start and end events; and the wakefulness detector 7280 issues start and end events of three types of wakefulness: short-term awake, long-term awake type 1, and long-term awake type 2. The three detectors are described in more detail below.

The detectors 7260 to 7280 may be said to operate in parallel. In this regard, the discrete logic of the process of a detector may have an apparent or actual simultaneous performance (e.g., parallel computing, parallel processing, multithreading, etc.) with the discrete logic of the process of one or more of the other detectors.

It should be understood that the feature calculations in steps 7210 to 7250 are continuous rather than one-off, to support the continuing operation of the three detectors 7260 to 7280. In other words, the feature calculations in steps

7210 to 7250 may be said to operate in parallel with the detectors 7260 to 7280, continually updating their various outputs, rather than preceding the detectors in a strict sequence. In this regard, the discrete logic of the process of the steps 7210 to 7250 may have an apparent or actual simultaneous performance (e.g., parallel computing, parallel processing, multithreading, etc.) with the discrete logic of the process of one or more of the detectors 7260 to 7280.

5.4.4.2.1 Sleep Onset Detector

During the onset of non-REM sleep, breathing transitions from being highly variable to semi-stable. The sleep onset detector 7260 therefore uses the slow consolidated variance feature Slow_Var_xform as an indicator of breath feature stability to infer the onset of non-REM sleep. In one implementation, the sleep onset detector 7260 looks for each of three successively easier conditions: breath features stable for a long period, breath features stable for the long period without a significant interval of instability during that period, and breath features not very unstable for the long period without a significant very unstable interval during that period.

FIG. 7E is a flow chart illustrating a method 7400 that may be used to implement the sleep onset detector 7260 in one form of the present technology. The method 7400 starts at step 7410, which waits for the ventilation ratio VR (computed by the ventilation determination algorithm 4322) to stabilise. (In other implementations, alternatives to using ventilation ratio in step 7410 could include using tidal volume $V_T$, peak flow rate Qpeak, mean respiratory flow rate Qr, etc.)

One implementation of step 7410 keeps the ventilation ratio VR of the last few breaths (e.g. 30 breaths) in a buffer, and finds the difference between the averages of the ventilation ratios of the first five breaths and the last five breaths in the buffer. The ventilation ratio VR is deemed to have stabilised if this difference is lower than a threshold (e.g. 0.25) for more than a certain number of consecutive breaths (e.g. five).

Step 7420 then waits for the slow consolidated variance feature Slow_Var_xform to rise and remain above a "stable" threshold (e.g. 10) for a "long" period (e.g. five minutes). If Slow_Var_xform falls below the stable threshold during step 7420 ("N"), the method 7400 returns to step 7420. Step 7430 then waits for the slow consolidated variance feature Slow-_Var_xform to remain above the stable threshold for a long period (e.g. five minutes) without falling below the stable threshold for a significant continuous interval (e.g. two minutes). If Slow_Var_xform falls below the stable threshold for continuously longer than the significant continuous interval during step 7430 ("N"), the method 7400 returns to step 7420.

Step 7440 then waits for the slow consolidated variance feature Slow_Var_xform to remain above a "very unstable" threshold (e.g. 4) that is lower than the stable threshold for a long period (e.g. five minutes) without falling below the "very unstable" threshold for a significant continuous interval (e.g. two minutes). The method 7400 then concludes at step 7450 by issuing an NREM start event as the time at which Slow_Var_xform first went above the "stable" threshold (step 7420). (In alternative implementations, the current time, or some intermediate time could be used for the NREM start event). If Slow_Var_xform falls below the "very unstable" threshold for continuously longer than the significant continuous interval during step 7440 ("N"), the method 7400 returns to step 7420.

5.4.4.2.2 REM Sleep Detector

REM sleep can be split into two components: Phasic REM, and tonic REM. It is during the phasic component of REM that breathing can be noticed to be varying most. On the whole, breathing during REM sleep will typically be more variable than during NREM sleep, but less variable than during wakefulness. However in some patients who experience more phasic REM, the variability will be increased, whilst in those that do not, the converse will happen.

In one implementation of the present technology, REM sleep is inferred when short- and medium term variation in tidal volume ($V_T$) and inter-breath intervals (TSLB) is observed, but overall breath features remain stable over the long term. Although in typical patients, such a short-term to long-term comparison may indicate REM sleep, there may be exceptions to this (e.g. NREM sleep instability—related to CAP sleep, Periodic Leg Movement, Restless Legs Syndrome).

FIGS. 7H and 7I together contain a flow chart illustrating a method 7700 that may be used to implement the REM sleep detector 7270 in one form of the present technology.

The method 7700 starts at step 7705, which waits until the patient has been asleep for a "settling period". This information may be obtained by monitoring NREM start events from the sleep onset detector 7260. The assumption here is that the patient will not go into a REM period straight after going to sleep. In one implementation this "settling period" is set to 15 minutes. In other implementations, the "settling period" may be dependent on the history of sleep stages during the session. Step 7710 follows, at which the method 7700 calculates upper and lower thresholds on tidal volume $V_T$. The lower tidal volume threshold is simply the threshold VT_REM_Booster_Threshold calculated at step 7250. The upper tidal volume threshold is some fixed increment or ratio greater than the lower tidal volume threshold. The next step 7720 checks whether the patient has been asleep for a "learning" period since the end of the "settling period" of step 7705. In one implementation the learning period is set to 30 minutes, but in other implementations it may range between 15 and 45 minutes. If not ("N"), the step 7725 learns thresholds for the fast VT and TSLB transformed variance features Fast_VT_xform and Fast_TSLB_xform. The thresholds represent "typical" or "natural" values of the respective features during the "learning" period and may be learnt from histograms of the respective features by a conventional statistical technique.

After the "learning" period has ended ("Y" at step 7720), step 7715 calculates a ratio REMRatio of "REM-like" breaths to all breaths since the end of the "settling period". A REM-like breath is characterised as one of a series of breaths during which there is a mild to moderate amount of instability in:

Slow_Var_xform
Slow_TSLB_xform, and
Slow_VT_xform

After step 7715, step 7730 checks whether the REM sleep detector 7270 is in a refractory period, during which REM sleep may not be detected. If it is ("Y"), step 7745 determines whether the refractory period has timed out. If not ("N"), the method 7700 concludes at step 7770. If it has ("Y"), step 7755 ends the refractory period before the concluding step 7770.

If the REM sleep detector 7270 is not in the refractory period ("N" at step 7730), step 7735 determines whether REMRatio computed at step 7715 is above a REM threshold indicating a preponderance of REM-like recent breaths, set in one implementation to 0.49. If so ("Y"), step 7750 determines whether the REM sleep detector 7270 is not in a provisional REM (PREM) state, and the RES_Event-_Counter (from the respiratory event pathway 7010) is less than or equal to 3, indicating that there have not been many recent RES events. If so ("Y"), step 7760 enters the PREM state and proceeds to step 7805 (FIG. 7I), recording the time of entry to the PREM state; otherwise ("N"), the method 7700 proceeds directly to step 7805.

If REMRatio did not indicate a preponderance of REM-like recent breaths ("N" at step 7735), the method 7700 determines at step 7740 whether the REM sleep detector 7270 is in the PREM state already. If not ("N"), the method 7700 concludes at step 7752. If so ("Y"), step 7765 updates a counter VT_10_Breath_Diff Above Thresh based on a comparison of the tidal volume difference feature VT_10_Breath_Diff with the upper and lower VT thresholds calculated at step 7710. In one implementation, step 7765 counts the number of excursions VT_10_Breath_Diff makes above the lower tidal volume threshold. In another implementation, step 7765 counts the number of times VT_10_Breath_Diff is within a range from the lower tidal volume threshold to the upper tidal volume threshold. The method 7700 proceeds to step 7810 (FIG. 7I).

Step 7805 determines whether the REM sleep detector 7270 has been in the PREM state for a long time, e.g. more than 30 minutes. If so ("Y"), step 7815 confirms the REM state and issues a REM start event set to the time of entry to the PREM state recorded at step 7760. Otherwise ("N"), or following step 7815, step 7830 again determines whether the REM sleep detector 7270 is in the PREM state. If so ("Y"), step 7835 updates the counter VT_10_Breath_Diff Above Thresh as described above in relation to step 7765. Otherwise ("N"), or following step 7835, the method 7700 concludes at step 7840.

Step 7810 determines whether the REM sleep detector 7270 has been in the PREM state for only a short time, in one implementation equal to less than 2 minutes. If so ("Y"), step 7825 exits the PREM state and clears the counter VT_10_Breath_Diff_Above_Thresh, as the period of REM-like preponderance was too short to count as a true REM sleep stage. Step 7865 then concludes the method 7700. Otherwise ("N"), step 7820 determines whether REMRatio has been below the REM threshold (from step 7735) continuously for a significant period, in one implementation set to 5 minutes. If not ("N"), the method 7700 concludes at step 7865 and the REM sleep detector 7270 remains in the PREM state. Otherwise ("Y"), step 7845 checks whether the REM sleep detector 7720 has been in the PREM state for a long time, set in one implementation to 10 minutes. If not ("N"), method 7700 proceeds to step 7825 to exit the PREM state and clear the VT_10_Breath_Diff_Above_Thresh counter as described above, as the period of REM-like preponderance was too short to count as a true REM sleep stage. Otherwise ("Y"), step 7850 calculates a REM tidal volume ratio threshold REMVTRatioThresh. In one implementation, step 7850 simply sets REMVTRatioThresh to 0.5. In other implementations, step 7850 sets REMVTRatioThresh to generally increase with the values of the counter VT_10_Breath_Diff_Above_Thresh and the threshold VT_REM_Booster_Threshold. FIG. 7K is an illustration of one such implementation of step 7850, whereby the VT_R-EM_Booster_Threshold/ VT_10_Breath_Diff_Above_Thresh plane is partitioned into rectangular regions, each of which corresponds to a value of REMVTRatioThresh. For example, in the region in which VT_REM_Booster_Threshold is between 0.02 and 0.03, and the counter VT_10_Breath_Diff_Above_Thresh is above 15, REMVTRatioThresh is set to 0.5.

Step 7855 then confirms the REM state if the ratio of the VT_10_Breath_Diff_Above_Thresh counter (calculated repeatedly during the PREM state as described above) to the total number of VT_10_Breath_Diff updates exceeds the threshold REMVTRatioThresh calculated at step 7850, and issues REM start and end events if the REM state is confirmed. The REM start event is the time of entry to PREM state recorded at step 7760, and the REM end event is the current time less the "significant period" used at step 7820, e.g. five minutes. Step 7860 then clears the VT_10_Breath_Diff_Above_Thresh counter and enters the refractory period described above, before the method 7700 concludes at step 7865.

5.4.4.2.3 Wakefulness Detector

When a patient is awake, breathing behaviour tends to be chaotic and is unlikely to display any specific behaviour. A patient may experience brief moments of wakefulness during the night or prolonged periods lasting a few hours. Given that a patient may be awake for less than 5 breaths or for well over 3 minutes, the wakefulness detector 7280 is implemented using two parallel pathways:

Short-term awake

Long-term awake

The short-term awake pathway is used in order to detect short bursts of awareness while a patient is still asleep. Both awake pathways are looking for large variation in the inter-breath intervals (TSLB), higher amplitude variation in tidal volume $V_T$, and changing expiratory flow shapes (NEPL). The short-term awake pathway looks for such variation in the short term, as indicated by a fall in the "fast" consolidated variance feature Fast_Var_xform. The long-term awake pathway looks for such variation in the long term, as indicated by a fall in the "slow" consolidated variance feature Slow_Var_xform.

A period of breathing instability could be a result of the patient being awake, or the patient being asleep but experiencing frequent respiratory events. Given that both scenarios present with similar breathing variability, the risk of misclassification is quite high. In order to lower the risk of misclassification, in addition to having a parallel respiratory event pathway 7010 (see FIG. 7A), the long-term awake pathway issues two types of long-term awake events: Long-Term Awake Type 1 (LTA_Type-1) and Long-Term Awake Type 2 (LTA_Type-2). The main difference between Type 1 and Type 2 is that the latter has an additional condition imposed on it, based on the medium-term variability of TSLB, as encapsulated in the TSLB_10_Breath_Diff feature. A persistently high value of TSLB_10_Breath_Diff indicates that the breathing instability is due to a true awakening, as opposed to frequently occurring respiratory events. An LTA_Type-2 event is therefore issued, which takes priority over both RES events and LTA_Type-1 events, as described below.

FIG. 7F is a state diagram illustrating a state machine 7500 that may be used to implement the short-term awake pathway of the wakefulness detector 7280 in one form of the present technology.

The state machine 7500 starts in an initial state 7505. The state machine 7500 transitions to a provisional short-term awake (PSTA) state 7510 upon the slow and fast consolidated variance features Slow_Var_xform and Fast_Var_xform falling below respective thresholds (e.g. 20 and 8), indicating some instability in breathing associated with short-term wakefulness. Once in the PSTA state 7510, the state machine 7500 starts a PSTA counter and sets a variable STA start time to the current time. If Slow_Var_xform returns above its threshold (e.g. 20), the state machine 7500 either returns to the initial state 7505, resetting all counters, or transitions to a confirmed short-term awake (CSTA) state 7515 to confirm a short-term awake event based on the PSTA counter and the following rules:

If the PSTA counter is less than 30 seconds, the state machine 7500 returns to the initial state 7505.

If the PSTA counter is greater than 45 seconds, the state machine transitions to the CSTA state 7515.

If the PSTA counter is greater than 30 seconds, but less than 45 seconds, then check to see if the Fast_Var_xform is greater than an upper threshold (eg. 20). If it is, the state machine exits the PSTA state 7510 and returns to the initial state 7505. If it is not (i.e. Fast_Var_xform is less than the upper threshold), the state machine transitions to the CSTA state 7515.

If Fast_Var_xform returns above its threshold (e.g. 8), and the PSTA counter is less than 15 seconds, the state machine 7500 returns to the initial state 7505, resetting all counters. If, however, Fast_Var_xform returns above its threshold (e.g. 8), and the PSTA counter is greater than 15 seconds, the state machine 7500 enters a provisional escape state (PES) 7525. Once in the provisional escape state 7525, the state machine 7500 starts a PES counter.

While in the provisional escape state 7525, if the PSTA counter is less than a threshold (e.g. 2 minutes), the state machine 7500 remains in the provisional escape state 7525 until one of the following conditions are met:

If the PES counter is less than 30 seconds and Fast_Var_xform drops below a lower threshold (e.g. 5), the state machine exits the provisional escape state 7525 and returns to the initial state 7505.

If the PES counter is greater than 30 seconds, and the PSTA counter is less than 30 seconds, the state machine exits the provisional escape state 7525 and returns to the initial state 7505.

If the PES counter is greater than 30 seconds and the PSTA counter is greater than 30 seconds, but less than 45 seconds, check to see if Fast_Var_xform is greater than an upper threshold (eg. 20). If it is, the state machine 7500 exits the provisional escape state 7525 and returns to the initial state 7505. If it is not (i.e. Fast_Var_xform is less than the upper threshold), the state machine 7500 transitions to CSTA state 7515 to confirm an STA event.

If the PES counter is greater than 30 seconds and the PSTA counter is greater than 45 seconds, the state machine 7500 transitions to CSTA state 7515 to confirm an STA event.

On the other hand, while in the provisional escape state 7525, if the PSTA counter is greater than the threshold (e.g. 2 minutes), the state machine 7500 remains in the provisional escape state 7525 until one of the following conditions are met:

If the PES counter is less than 30 seconds and Fast_Var_xform drops below a threshold (e.g. 5), the state machine exits the provisional escape state 7525 and returns to the initial state 7505.

If the PES counter is greater than 30 seconds and a ratio FastTSLBRatio is greater than a set threshold (e.g. 0.75), the state machine 7500 transitions to CSTA state 7515 to confirm an STA event. (The ratio FastTSL-BRatio is the ratio of the number of TSLB_10_Breath_Diff values above a set threshold (e.g. 0.4) to the total number value of TSLB_10_Breath_Diff values computed during the PSTA and provisional escape states.)

If the PES counter is greater than 30 seconds and the FastTSLBRatio is less than a set threshold (eg. 0.75), the state machine exits the provisional escape state 7525 and returns to the initial state 7505.

In the CSTA state 7515, the state machine 7500 issues an STA start event and an STA end event. The STA start event is the value STA start time mentioned above, and the STA end event is the current time less the value of the PES counter. The state machine 7500 then returns to the initial state 7505.

FIG. 7G is a state diagram illustrating a state machine 7600 that may be used to implement the long-term awake pathway of the wakefulness detector 7280 in one form of the present technology. The state machine 7600 operates in parallel with the short-term awake pathway state machine 7500.

The state machine 7600 starts in an initial state 7605. The state machine 7600 transitions to a provisional long-term awake (PLTA) state 7610 upon the slow consolidated variance feature Slow_Var_xform falling below a threshold indicating some instability in breathing associated with wakefulness. In one implementation, this threshold is a fixed value, e.g. 5. In other implementations, this threshold is equal to Slow_Var_xform_Threshold_Filtered, as computed at step 7250. In some implementations, the threshold can be adjusted to accommodate sleep instability as follows: a sleep stability index is calculated based on the Slow_Var_xform histogram. The threshold is adjusted based on the sleep stability index, e.g. if there is a lot of instability, the threshold may be reduced by a factor of 0.5. If there is only moderate instability, the threshold may be reduced by a factor of 0.25.

Once in the PLTA state 7610, the state machine 7600 starts a PLTA counter and sets a variable LTA_start_time to the current time. If Slow_Var_xform returns above the threshold mentioned above, the state machine 7600 returns to the initial state 7605, resetting all counters. A confirmed LTA (CLTA) state 7615 is entered once the PLTA counter exceeds a threshold (equal to 60 seconds in one implementation). For each breath in the PLTA state 7610, three variables known as VT_trend_counter, awakeTSLBCounter, and awakeTSLBRatio are updated. VT_trend_counter is an indication that the short-term tidal volume trend feature Short_Term_VT_Trend is significantly greater than the long term trend feature Long_Term_VT_Trend (both of which are calculated at step 7240). Such an indication is useful since for certain patients the ratio tends to increase rapidly when the patient awakens, and stay high while the patient hyperventilates until they fall asleep, when the ratio falls again. As long as the ratio is high, the patient is likely to be awake, even though their breathing is stable, which would otherwise indicate a return to sleep. In one implementation, VT_trend_counter is a binary variable that is set to one when the ratio of Short_Term_VT_Trend to Long_Term_VT_Trend is greater than a threshold, e.g. 1.5, and to zero otherwise.

The value of awakeTSLBCounter is the number of times Fast_TSLB_xform exceeds the threshold TSLB Awake Threshold computed at step 7250, and the value of awakeTSLBRatio is the ratio of awakeTSLBCounter to the number of updates of Slow_TSLB_xform.

If while in the CLTA state 7615, Slow_Var_xform exceeds the threshold above, indicating a return to breathing stability, the state machine 7600 enters a provisional back to sleep (PBTS) state 7635. If while in the PBTS state 7635

Slow_Var_xform falls below the threshold, indicating breathing instability, the state machine 7600 returns to the CLTA state 7615.

Once the state machine 7600 has remained in the PBTS state 7635 for more than 60 seconds, the state machine 7600 enters a confirmed back to sleep (CBTS) state 7640, and records the current time as the variable CBTS_entry_time. The state machine 7600 transitions out of the CBTS state 7640 upon one of three conditions occurring. Condition 1 occurs when the following criteria hold:

Current time minus LTA_start_time is less than three minutes, and

VT_trend_counter is zero.

Upon condition 1 occurring during the CBTS state 7640, the state machine 7600 decides the wake period was too short to qualify as long-term awake, and returns to the initial state 7605, resetting all counters.

Condition 2 occurs when the following criteria hold:

Current time minus LTA_start_time exceeds three minutes, and

VT_trend_counter is zero.

Upon condition 2 occurring during the CBTS state 7640, the state machine 7600 proceeds to step 7650, which issues an LTA event of either type 1 or type 2, as follows. If the elapsed time in the CLTA state exceeds 2.5 minutes (i.e. the PLTA counter exceeds 3.5 minutes), the awakeTSLBRatio exceeds 0.5, and the awakeTSLBcounter exceeds 2, an LTA-1 event has occurred. The state machine 7600 therefore issues an LTA-1 start event equal to LTA_start_time, and an LTA-1 end event equal to the current time minus 60 seconds. If, otherwise, the elapsed time in the CLTA state exceeds 5 minutes (i.e. the PLTA counter exceeds 6 minutes), the state machine 7600 issues an LTA-1 start event equal to LTA_start_time, and an LTA-1 end event equal to the current time minus 60 seconds. If, furthermore, the awakeTSLBRatio exceeds 0.7, and the awakeTSLBcounter exceeds 9, an LTA-2 event has occurred. The state machine 7600 therefore issues an LTA-2 start event equal to LTA_start_time, and an LTA-2 end event equal to the current time minus 60 seconds.

Condition 3 occurs when the following criteria hold:

VT_trend_counter is equal to 1, i.e. the tidal volume short-term to long-term trend was unstable.

The ratio of Short_Term_VT_Trend to Long_Term_VT_Trend then drops to less than a threshold, e.g. 1.5.

Upon condition 3 occurring during the CBTS state 7640, the state machine 7600 proceeds to step 7650 to issue an LTA event as described above.

After step 7650, the state machine 7600 returns to the initial state 7605, resetting all counters.

5.4.4.3 Event Combination

As mentioned above, step 7050 of the method 7000 combines the RES and non-RES start/end events 7030 and 7040 to produce a four-valued indication 7060 of a sleep stage of the patient 1000. Such an indication may be output by an apparatus/processor in various forms.

The operation of step 7050 differs depending on whether the method 7000 is a real-time or a post-processing implementation of the sleep stage inference algorithm 4328. In a post-processing implementation, step 7050 may store the events in time order and generate the indications 7060 for the entire session in a four-valued hypnogram. The starting point for such a detection implementation is to assume the patient was in deep (NREM) sleep at all times during the session. The start/end events of each stage of sleep are then consolidated into the hypnogram, or other output representation such as for storage in a memory or display, in the following order of priority (lowest priority first):

REM start/end

Short-term awake (STA) start/end

Long-term awake type 1 (LTA-1) start/end

RES start/end

Long-term awake type 2 (LTA-2) start/end

NREM start (sleep onset)

Each event of higher priority overwrites any overlapping sections on the hypnogram with a section of the corresponding sleep stage. In this regard, the pathways of the detectors may result in detections of sleep stage that are contradictory (e.g., detection collision of two or more different stages overlapping in time in whole or in part.) However, priorities, which may be predetermined, are applied by the system to resolve such detection collisions of sleep stage indication, such that the higher priority detection prevails. In this regard, a detection of a stage of higher priority may cause some or all of a detection of a stage of lower priority to be disregarded.

FIG. 8 contains an example graph 8000 illustrating the post-processing implementation of step 7050 described above. The top trace 8010 shows a hypnogram consisting of deep (NREM) sleep throughout the session, which is the default sleep stage. The next trace 8020 shows two pairs of REM start and end events. Trace 8030 shows four STA start/end event pairs. Trace 8040 shows two pairs of LTA-1 start/end events. Trace 8050 shows two pairs of RES start/end events. Trace 8060 shows an LTA-2 start event near the end of the session. Trace 8070 shows an NREM start event near the start of the session. The final trace 8080 is the hypnogram in which all the events from traces 8020 to 8070 are combined into a four-valued indication of sleep stage.

A real-time implementation of the event combination step 7050 acts in analogous fashion to the post-processing implementation described above. The default sleep stage is NREM sleep. In a real-time implementation, step 7050 may store the generated indications 7060 in time order in a four-valued hypnogram representing the sleep session.

5.4.4.4 Accuracy of Sleep Stage Inference

The method 7000 described above was developed and trained by processing 146 respiratory flow rate signals recorded by an RPT device during respective polysomnography (PSG) sessions. The method 7000 was then validated by processing a further 83 respiratory flow rate signals, also recorded by an RPT device during respective PSG sessions. The resulting hypnograms were compared against scoring of the PSG data by human experts.

The overall agreement between PSG scoring and the resulting hypnograms during the respective training and validation phases was 81.55% (CI=79.6%, 83.4%) and 84.3% (CI=81.3%, 87.5%).

5.4.4.5 Use of Sleep Stage Indications by Therapy Control Module

As mentioned above, the therapy control module 4330 may use the indications of sleep stage returned by real-time forms of the sleep stage inference algorithm 4328 to influence the therapy delivered to the patient. In some forms, the therapy control module 4330 alters the treatment pressure Pt or the mask pressure Pm depending on the indications.

For example, at the start of therapy, the therapy control module 4330 may hold the mask pressure Pm at a subtherapeutic pressure Psub until sleep onset is detected by the sleep onset detector 7260, at which point the therapy control module 4330 may increase the mask pressure Pm to a treatment pressure Pt via a bridging profile, as described in PCT Publication number WO 2015/131219.

In another example, the therapy control module 4330 may not decrease the treatment pressure Pt during episodes of REM sleep, where otherwise the therapy control module 4330 may have decreased the treatment pressure Pt in the absence of indications of SDB events.

In yet another example, the therapy control module 4330 may decrease the treatment pressure Pt during short-term or long-term awake episodes, to assist the patient in returning to sleep.

In yet another example, the therapy control module 4330 may search for a value of treatment pressure Pt that results in "stable sleep", as evidenced by the absence of RES or awake states, and may subsequently ensure that the pressure does not fall below this value.

5.5 Glossary

For the purposes of the present technology disclosure, in certain forms of the present technology, one or more of the following definitions may apply. In other forms of the present technology, alternative definitions may apply.

5.5.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Leak: The word leak will be taken to be an unintended flow of air. In one example, leak to the ambient may occur as the result of an incomplete seal between a mask and a patient's face. In another example leak to the ambient may occur in a swivel elbow.

Patient: A person, whether or not they are suffering from a respiratory disorder.

Pressure: Force per unit area. Pressure may be expressed in a range of units, including $cmH_2O$, g-f/cm$^2$ and hectopascal. 1 $cmH_2O$ is equal to 1 g-f/cm$^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.5.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory airflow rate, as opposed to "true respiratory flow rate" or "true respiratory airflow rate", which is the actual respiratory flow rate experienced by the patient, usually expressed in litres per minute.

Tidal volume ($V_T$): The volume of air inhaled or exhaled by each breath during normal breathing, when extra effort is not applied. The inspiratory tidal volume ($V_I$) (the inhaled volume) and the expiratory tidal volume ($V_E$) (the exhaled volume) may be measured directly, in which case the tidal volume $V_T$ may be computed as the average of these quantities.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.6 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.7 Reference Signs List patient 1000
bed partner 1100
patient interface 3000
seal-forming structure 3100
plenum chamber 3200
structure 3300
vent 3400
connection port 3600
forehead support 3700
RPT device 4000
external housing 4010
upper portion 4012
portion 4014
panel 4015
chassis 4016
handle 4018
pneumatic block 4020
pneumatic components 4100
air filter 4110
inlet air filter 4112
outlet air filter 4114
mufflers 4120
inlet muffler 4122
outlet muffler 4124
pressure generator 4140
blower 4142
motor 4144
anti-spill back valve 4160
air circuit 4170
supplemental oxygen 4180
electrical components 4200
PCBA 4202
power supply 4210
input device 4220
central controller 4230
clock 4232
therapy device controller 4240
protection circuits 4250
memory 4260
transducers 4270
pressure sensor 4272
flow rate sensor 4274
motor speed transducer 4276
data communication interface 4280
remote external communication network 4282
local external communication network 4284
remote external device 4286
local external device 4288
output devices 4290
display driver 4292
display 4294
algorithms 4300
pressure compensation algorithm 4312
vent flow rate estimation algorithm 4314
leak flow rate estimation algorithm 4316
respiratory flow rate estimation algorithm 4318
breath framing algorithm 4321
ventilation determination algorithm 4322
inspiratory flow limitation determination algorithm 4323
RERA detection algorithm 4324 apnea/hypopnea detection algorithm 4325
jamming determination algorithm 4326
airway patency determination algorithm 4327
sleep stage inference algorithm 4328
therapy parameter determination algorithm 4329
therapy control module 4330
humidifier 5000
method 7000
respiratory event pathway 7010
breathing stability pathway 7020
RES start/end events 7030
non-RES start/end events 7040
step 7050
four-valued indication 7060
method 7100
step 7105
step 7110
step 7115
step 7120
step 7125
step 7130
step 7135
step 7140
step 7150
step 7155
step 7160
step 7165
method 7200
step 7210
step 7220
step 7225
step 7230
step 7240
step 7250
sleep onset detector 7260
REM sleep detector 7270
wakefulness detector 7280
method 7300
method 7300A
step 7310
step 7320
step 7330
step 7340
step 7350
step 7360
method 7400
step 7410
step 7420
step 7430
step 7440
step 7450
state machine 7500
initial state 7505
PSTA state 7510
CSTA state 7515
provisional escape state 7525
state machine 7600
initial state 7605
PLTA state 7610
CLTA state 7615
PBTS state 7635
CBTS state 7640
step 7650
method 7700
step 7705
step 7710
step 7715 step 7720
step 7725
step 7730
step 7735
step 7740
step 7745
step 7750
step 7752
step 7755
step 7760
step 7765
step 7770
step 7805
step 7810
step 7815
step 7820
step 7825
step 7830
step 7835
step 7840
step 7845
step 7850
step 7855
step 7860
step 7865
state machine 7900
state 7910
state 7920
graph 8000
trace 8010
trace 8020
trace 8030
trace 8040
trace 8050
trace 8060
trace 8070
trace 8080

The invention claimed is:

1. A method of indicating wakefulness of a patient, the method comprising:

applying, in a wakefulness detector of one or more processors, first and second parallel detection pathways to breath features derived from a signal representing a respiratory flow rate of the patient;

in each of the first and second parallel detection pathways, assessing the breath features, wherein the first parallel detection pathway is configured to evaluate variation of the breath features in a short term and wherein the second parallel detection pathway is configured to evaluate variation of the breath features in a long term; and generating, from the wakefulness detector of the one or more processors, start events and end events from the evaluations of the first parallel detection pathway and the second parallel detection pathway to produce indications of wakefulness of the patient.

2. The method of claim 1, wherein the breath features comprise at least one of: (a) inter-breath intervals, (b) tidal volume, and (c) expiratory flow shape.

3. The method of claim 1, wherein the produced indications of wakefulness comprise an indication of short-term awake from the first parallel detection pathway and an indication of long-term awake from the second parallel detection pathway.

4. The method of claim 3, wherein the indication of long-term awake comprises generating indications of first and second types of long-term awake.

5. The method of claim 1, wherein the first parallel detection pathway is a state machine having a plurality of states comprising: an initial state, a provisional short-term awake state, a provisional escape state and a confirmed short-term awake state.

6. The method of claim 1, wherein the second parallel detection pathway is a state machine having a plurality of states comprising: an initial state, a provisional long-term awake state, a provisional back-to-sleep state, a confirmed back-to-sleep state and a confirmed long-term awake state.

7. The method of claim 1, wherein the wakefulness detector generates a short-term awake start event on detecting large short-term variation in the breath features.

8. The method of claim 1, wherein the wakefulness detector generates a long-term awake start event on detecting large long-term variation in the breath features.

9. The method of claim 8, wherein the wakefulness detector generates a long-term awake start event of a second type on detecting medium-term variability of a breath feature.

10. A computer processor-readable memory storage apparatus having processor-executable instructions encoded thereon which, when executed by one or more processors, control the one or more processors to perform a method of indicating wakefulness of a patient, the processor-executable instructions comprising:

instructions to apply, in a wakefulness detector of one or more processors, first and second parallel detection pathways to breath features derived from a signal representing a respiratory flow rate of the patient;

instructions to assess, in each of the first and second parallel detection pathways, the breath features, wherein the first parallel detection pathway is configured to evaluate variation of the breath features in a short term and wherein the second parallel detection pathway is configured to evaluate variation of the breath features in a long term; and instructions to generate, from the wakefulness detector of the one or more processors, start events and end events from the evaluations of the first parallel detection pathway and the second parallel detection pathway to produce indications of wakefulness of the patient.

11. The computer processor-readable memory storage apparatus of claim 10, wherein the breath features comprise at least one of: (a) inter-breath intervals, (b) tidal volume, and (c) expiratory flow shape.

12. The computer processor-readable memory storage apparatus of claim 10, wherein the produced indications of wakefulness comprise an indication of short-term awake from the first parallel detection pathway and an indication of long-term awake from the second parallel detection pathway.

13. The computer processor-readable memory storage apparatus of claim 12, wherein the indication of long-term awake comprises generating indications of first and second types of long-term awake.

14. The computer processor-readable memory storage apparatus of claim 10, wherein the first parallel detection pathway is a state machine having a plurality of states comprising: an initial state, a provisional short-term awake state, a provisional escape state and a confirmed short-term awake state.

15. The computer processor-readable memory storage apparatus of claim 10, wherein the second parallel detection pathway is a state machine having a plurality of states comprising: an initial state, a provisional long-term awake state, a provisional back-to-sleep state, a confirmed back-to-sleep state and a confirmed long-term awake state.

16. The computer processor-readable memory storage apparatus of claim 10, wherein the wakefulness detector generates a short-term awake start event on detecting large short-term variation in the breath features.

17. The computer processor-readable memory storage apparatus of claim 10, wherein the wakefulness detector generates a long-term awake start event on detecting large long-term variation in the breath features.

18. The computer processor-readable memory storage apparatus of claim 17, wherein the wakefulness detector generates a long-term awake start event of a second type on detecting medium-term variability of a breath feature.

19. An apparatus comprising:

a sensor configured to generate a signal representing a property of a flow of air within a patient interface configured to engage with an entrance to an airway of a patient; and one or more processors configured to receive the signal and further configured to:

apply, in a wakefulness detector of one or more processors, first and second parallel detection pathways to breath features derived from the signal;

in each of the first and second parallel detection pathways, assess the breath features, wherein the first parallel detection pathway is configured to evaluate variation of the breath features in a short term and wherein the second parallel detection pathway is configured to evaluate variation of the breath features in a long term; and generate, from the wakefulness detector of the one or more processors, start events and end events from the evaluations of the first parallel detection pathway and the second parallel detection pathway to produce indications of wakefulness of the patient.

20. The apparatus of claim 19, further comprising: a pressure generator configured to generate a supply of air at positive pressure to an airway of the patient via the patient interface over an air circuit, wherein the one or more processors is/are configured to control the supply of air based on the wakefulness indicated.

21. The apparatus of claim 19, wherein the sensor is located within the patient interface and the property is pressure.

22. The apparatus of claim 21, wherein the one or more processors is/are located within the patient interface.

23. The apparatus of claim 21, wherein the one or more processors is/are located in a remote external computing device configured to communicate with the patient interface.

24. The apparatus of claim 19, further comprising:

a pressure generator configured to generate a supply of air at positive pressure to an airway of the patient via the patient interface over an air circuit, and a central controller configured to control the pressure generator, and, wherein:

(a) the one or more processors is/are the central controller; or (b) the one or more processors is/are located in a remote external computing device configured to communicate with the central controller.

25. The apparatus of claim 24, wherein the sensor is located within the pressure generator, and the property is flow rate.

26. The apparatus of claim 25, wherein the apparatus further comprises the patient interface.

27. The apparatus of claim 24, wherein the sensor is located within the air circuit, and the property is flow rate.

* * * * *